United States Patent
Hosoe et al.

(10) Patent No.: US 11,471,533 B2
(45) Date of Patent: Oct. 18, 2022

(54) COMPOUND USABLE AS CATIONIC LIPID

(71) Applicant: Kyowa Kirin Co., Ltd., Tokyo (JP)

(72) Inventors: Shintaro Hosoe, Tokyo (JP); Hayato Yabuuchi, Tokyo (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 629 days.

(21) Appl. No.: 16/336,668

(22) PCT Filed: Sep. 27, 2017

(86) PCT No.: PCT/JP2017/034878
§ 371 (c)(1),
(2) Date: Mar. 26, 2019

(87) PCT Pub. No.: WO2018/062233
PCT Pub. Date: Apr. 5, 2018

(65) Prior Publication Data
US 2021/0275672 A1 Sep. 9, 2021

(30) Foreign Application Priority Data

Sep. 27, 2016 (JP) .............................. JP2016-188681

(51) Int. Cl.
*A61K 47/18* (2017.01)
*A61K 9/00* (2006.01)
*C07C 217/28* (2006.01)
*C12N 15/113* (2010.01)

(52) U.S. Cl.
CPC ............ *A61K 47/18* (2013.01); *A61K 9/0019* (2013.01); *C07C 217/28* (2013.01); *C12N 15/113* (2013.01); *C12N 15/1137* (2013.01); *C12N 2310/14* (2013.01); *C12N 2320/32* (2013.01)

(58) Field of Classification Search
CPC .. A61K 31/713; A61K 31/7088; A61K 47/18; A61K 48/00; A61P 1/16; A61P 11/00; A61P 13/12; C12N 15/113
USPC ..................... 435/6.1, 91.1, 91.31, 455, 458; 514/44 A, 44 R; 536/23.1, 24.1; 424/9.1
See application file for complete search history.

(56) References Cited

U.S. PATENT DOCUMENTS

| | | | |
|---|---|---|---|
| 8,748,667 B2 | 6/2014 | Budzik et al. | |
| 8,802,863 B2 | 8/2014 | Budzik et al. | |
| 9,044,512 B2 | 6/2015 | Budzik et al. | |
| 9,062,021 B2 | 6/2015 | Budzik et al. | |
| 9,315,437 B2 | 4/2016 | Budzik et al. | |
| 9,643,916 B2 | 5/2017 | Budzik et al. | |
| 2013/0090372 A1 | 4/2013 | Budzik et al. | |
| 2013/0150625 A1 | 6/2013 | Budzik et al. | |
| 2014/0235872 A1 | 8/2014 | Budzik et al. | |
| 2014/0323548 A1 | 10/2014 | Budzik et al. | |
| 2015/0315112 A1 | 11/2015 | Budzik et al. | |
| 2016/0074471 A1* | 3/2016 | Ko ..................... C12Q 1/686 514/6.9 |
| 2017/0050917 A1 | 2/2017 | Budzik et al. | |

FOREIGN PATENT DOCUMENTS

| | | |
|---|---|---|
| JP | 9-255638 | 9/1997 |
| JP | 2013-531634 | 8/2013 |
| JP | 2013-533223 | 8/2013 |
| WO | 2009/129385 | 10/2009 |
| WO | 2010/042877 | 4/2010 |
| WO | 2010/054401 | 5/2010 |
| WO | 2011/149733 | 12/2011 |
| WO | WO-2012051301 A1 * 4/2012 ......... G01N 33/6893 |
| WO | 2012/108397 | 8/2012 |

OTHER PUBLICATIONS

Wang et al (Nature, vol. 16, pp. 678-698 (2015)) (Year: 2015).*
M. Hendricks (Johns Hopkins Medicine communication, The Mouse Model: Less than Perfect, Still Invaluable, https://www.hopkinsmedicine.org/institute_basic_biomedical_sciences/news_events/articles_and_stories/model_organisms/201010_mouse_model.html, pp. 1-3 (retrieved Apr. 7, 2022) (Year: 4722).*
Maier et al., "Biodegradable Lipids Enabling Rapidly Eliminated Lipid Nanoparticles for Systemic Delivery of RNAi Therapeutics," The American Society of Gene & Cell Therapy, Aug. 2013, vol. 21, No. 8, pp. 1570-1578.
Antipina et al., "Investigation of the Protonation State of Novel Cationic Lipids Designed for Gene Transfection," J. Phys. Chem., 2007, vol. 111, pp. 13845-13850.
Kim et al., "A New Dioleate Compound from Callistemon lanceolatus," Bull. Korean Chem. Soc., 2012, vol. 33, No. 1, p. 344-346.
International Search Report dated Nov. 14, 2017 in International (PCT) Application No. PCT/JP2017/034878.

* cited by examiner

*Primary Examiner* — Jane J Zara
(74) *Attorney, Agent, or Firm* — Wenderoth, Lind & Ponack, L.L.P.

(57) ABSTRACT

The present invention provides a compound represented by formula (I) usable as a cationic lipid that facilitates introduction of a nucleic acid, for example, into a cell, and a composition or the like containing the compound.

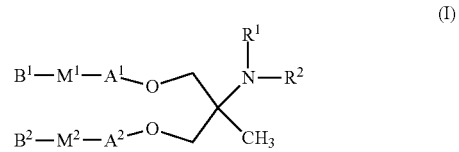

(I)

17 Claims, 1 Drawing Sheet
Specification includes a Sequence Listing.

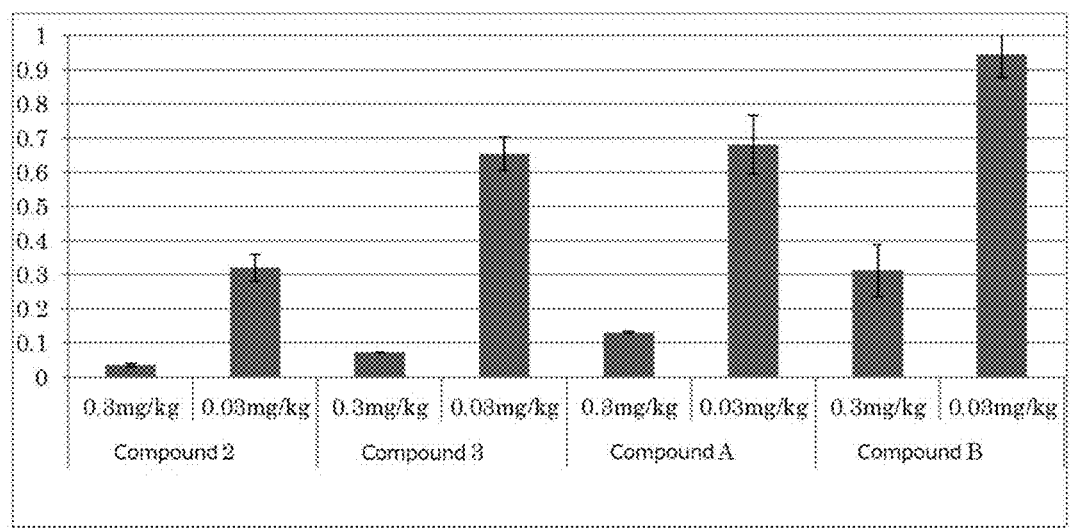

COMPOUND USABLE AS CATIONIC LIPID

TECHNICAL FIELD

The present invention relates to a novel compound usable as a cationic lipid, and a composition or the like containing the novel compound.

BACKGROUND ART

Cationic lipids are amphipathic molecules having a lipophilic region containing one or more hydrocarbon groups, and a hydrophilic region containing at least one positively charged polar head group. Cationic lipids are useful, because cationic lipids facilitate entry of macromolecules such as nucleic acids into the cytoplasm through the cell plasma membrane by forming a positively charged (total charge) complex with macromolecules such as nucleic acids. This process, performed in vitro and in vivo, is known as transfection.

Patent Literatures 1 to 4 disclose cationic lipids and lipid particles containing the cationic lipids, which are advantageous for delivering nucleic acids to cell in vivo, and for using nucleic acid-lipid particle compositions suitable for treatment of a disease.

Patent Literature 1 discloses cationic lipids, for example,

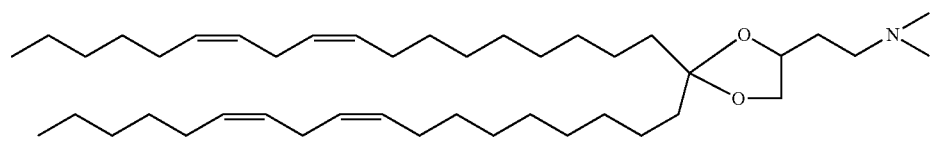 [SMILES: CCCCC/C=C\C/C=C\CCCCCCCCC1(CCCCCCCC/C=C\C/C=C\CCCCC)OCC(CCN(C)C)O1]

2,2-dilinoleyl-4-(2-dimethylaminoethyl)-[1,3]-dioxolane (DLin-KC2-DMA), and the like. Patent Literature 2 discloses cationic lipids, for example,

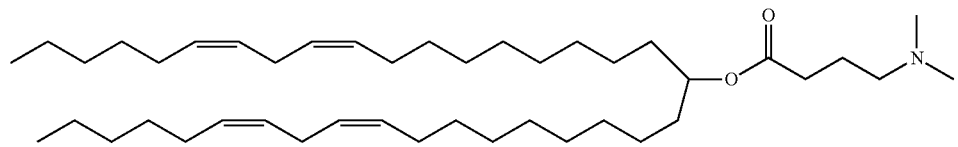 [SMILES: CCCCC/C=C\C/C=C\CCCCCCCCC(CCCCCCCC/C=C\C/C=C\CCCCC)OC(=O)CCCN(C)C]

(6Z,9Z,28Z,31Z)-heptatriaconta-6,9,28,31-tetraen-19-yl 4-(dimethylamino)butanoate (DLin-MC3-DMA), and the like. Patent Literature 3 discloses cationic lipids, for example,

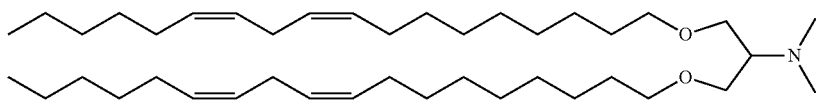 [SMILES: CCCCC/C=C\C/C=C\CCCCCCCCOCC(COCCCCCCCC/C=C\C/C=C\CCCCC)N(C)C]

N,N-dimethyl-N-(2-(((9Z,12Z)-octadeca-9,12-dienyloxy)-1-(((9Z,12Z)-octadeca-9,12-dienyloxy)methyl)ethyl)amine, and the like. Patent Literature 4 discloses cationic lipids, for example,

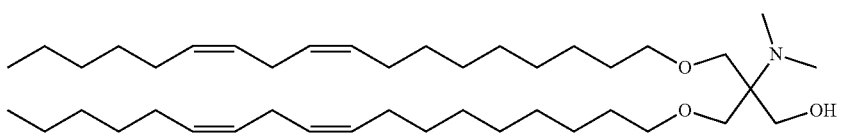 [SMILES: CCCCC/C=C\C/C=C\CCCCCCCCOCC(CO)(COCCCCCCCC/C=C\C/C=C\CCCCC)N(C)C]

2-(dimethyl)-3-[{(9Z,12Z)-octadeca-9,12-dien-1-yl}oxy]-2-([{(9Z,12Z)-octadeca-9,12-dien-1-yl}oxy]methyl)propan-1-ol, and the like.

Also, Non Patent Literature 1 discloses that toxicity in the liver can be reduced while keeping the capacity for delivering nucleic acids to cells in vivo by incorporating a biodegradable group into a part of a fatty chain of a cationic lipid, and discloses cationic lipids, for example,

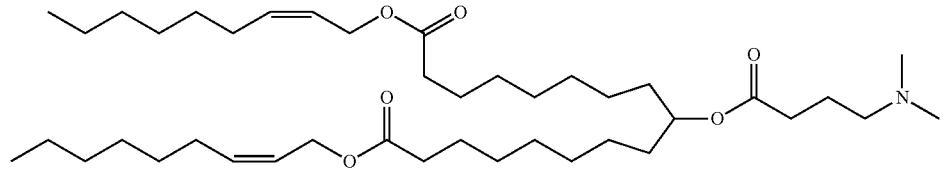 [SMILES: CCCCCC/C=C\COC(=O)CCCCCCCC(CCCCCCCC(=O)OC/C=C\CCCCCC)OC(=O)CCCN(C)C]

di[(Z)-non-2-en-1-yl]9-{[4-(dimethylamino)butanoyl]oxy}heptadecanedioate), and the like.

CITATION LIST

Patent Literature

Patent Literature 1: WO 2010/042877
Patent Literature 2: WO 2010/054401
Patent Literature 3: WO 2009/129385
Patent Literature 4: WO 2011/149733

Non Patent Literature

Non Patent Literature 1: Molecular Therapy, 2013, vol. 21, p. 1570-1578

SUMMARY OF THE INVENTION

Technical Problem

An object of the present invention is to provide a novel compound usable as a cationic lipid that facilitates introduction of a nucleic acid, for example, into a cell, and a composition or the like containing the novel compound.

Means for Solving the Problems

The present invention relates to the following (1) to (29):
(1) A compound represented by formula (I), or a pharmaceutically acceptable salt thereof:

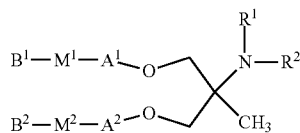

(I)

wherein $R^1$ and $R^2$ are, the same or different, a hydrogen atom or C1-C3 alkyl;
$A^1$ and $A^2$ are, the same or different, linear or branched C8-C20 alkylene or C8-C20 alkenylene;
$M^1$ and $M^2$ are, the same or different, selected from the group consisting of —C=C—, —OC(O)—, —C(O)O—, —SC(O)—, —C(O)S—, —OC(S)—, —C(S)O—, —SS—, —C($R^5$)=N—, —N=C($R^5$)—, —C($R^5$)=N—O—, —O—N=C($R^5$)—, —N($R^5$)C(O)—, —C(O)N($R^5$)—, —N($R^5$)C(S)—, —C(S)N($R^5$)—, —N($R^5$)C(O)N($R^6$)—, —N($R^5$)C(O)O—, —OC(O)N($R^5$)—, and —OC(O)O—;
$R^5$ and $R^6$ are, the same or different, a hydrogen atom or C1-C3 alkyl; and
$B^1$ and $B^2$ are, the same or different, linear or branched C1-C16 alkyl or C2-C16 alkenyl.

(2) The compound according to the above described (1), or a pharmaceutically acceptable salt thereof, wherein $R^1$ and $R^2$ are, the same or different, a hydrogen atom or methyl.
(3) The compound according to the above described (1) or (2), or a pharmaceutically acceptable salt thereof, wherein $A^1$ and $A^2$ are, the same or different, linear or branched C8-C12 alkylene or C10-C14 alkenylene.
(4) The compound according to any of the above described (1) to (3), or a pharmaceutically acceptable salt thereof, wherein $M^1$ and $M^2$ are, the same or different, selected from the group consisting of —C=C—, —OC(O)—, and —C(O)O—.
(5) The compound according to any of the above described (1) to (4), or a pharmaceutically acceptable salt thereof, wherein $B^1$ and $B^2$ are, the same or different, linear or branched C2-C9 alkyl or C3-C9 alkenyl.
(6) The compound according to any of the above described (1) to (5), or a pharmaceutically acceptable salt thereof, wherein $B^1$-$M^1$-$A^1$ and $B^2$-$M^2$-$A^2$ are, the same or different, selected from the group consisting of (Z)-tetradec-9-enyl, (Z)-hexadec-9-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, and (Z)-docos-13-enyl.
(7) The compound according to any of the above described (1) to (6), or a pharmaceutically acceptable salt thereof, wherein $B^1$-$M^1$-$A^1$ and $B^2$-$M^2$-$A^2$ are, the same or different, selected from the group consisting of (Z)-hexadec-9-enyl, (Z)-octadec-9-enyl, (9Z,12Z)-octadeca-9,12-dienyl, and (11Z,14Z)-icosa-11,14-dienyl.
(8) The compound according to any of the above described (1) to (5), or a pharmaceutically acceptable salt thereof,
wherein $B^1$-$M^1$-$A^1$ and $B^2$-$M^2$-$A^2$ are, the same or different, selected from the following structures:

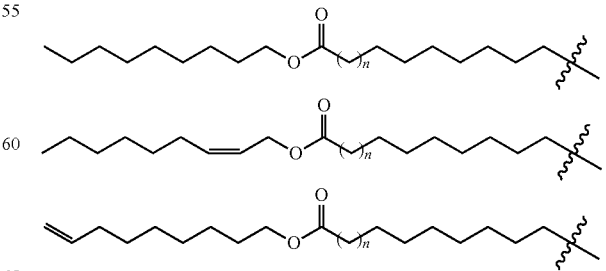

wherein n is an integer from 1 to 4.

(9) The compound according to any of the above described (1) to (8), or a pharmaceutically acceptable salt thereof, wherein $B^1$-$M^1$-$A^1$ and $B^2$-$M^2$-$A^2$ are the same.
(10) The compound according to any one of the above described (1) to (9), or a pharmaceutically acceptable salt thereof, which is a cationic lipid.
(11) A composition, comprising the compound according to any one of the above described (1) to (10) or a pharmaceutically acceptable salt thereof, and a nucleic acid.
(12) The composition according to the above described (11), wherein the compound or a pharmaceutically acceptable salt thereof and the nucleic acid together form a complex, or the composition further contains a neutral lipid and/or a polymer and the compound or a pharmaceutically acceptable salt thereof and the neutral lipid and/or the polymer together form a complex.
(13) The composition according to the above described (12), containing a lipid membrane, wherein the complex is enclosed with the lipid membrane.
(14) The composition according to any of the above described (11) to (13), wherein the nucleic acid is a nucleic acid having a silencing effect on a target gene through the use of RNA interference (RNAi).
(15) The composition according to the above described (14), wherein the target gene is a gene related to tumor.
(16) The composition according to the above described (14) or (15), wherein the target gene is a gene expressed in the liver, the lung, the kidney, or the spleen.
(17) A method for introducing the nucleic acid into a cell using a composition according to any of the above described (11) to (16).
(18) The method according to the above described (17), wherein the cell is a cell that resides in the liver, the lung, the kidney, or the spleen of a mammal.
(19) The method according to the above described (17) or (18), wherein the nucleic acid is introduced into a cell by intravenous administration of the composition.
(20) A treatment method for a disease, comprising a step of administering the composition according to any one of the above described (11) to (16) to a mammal.
(21) The method according to the above described (20), wherein the composition is intravenously administered.
(22) The method according to the above described (20) or (21), wherein the disease is a disease related to the liver, the lung, the kidney or the spleen.
(23) A medicament, comprising the compound according to any one of the above described (1) to (10) or a pharmaceutically acceptable salt thereof, and a nucleic acid.
(24) A medicament, comprising the composition according to any one of the above described (11) to (16).
(25) The medicament according to the above described (23) or (24), wherein the medicament is for intravenous administration.
(26) The medicament according to any one of the above described (23) to (25), for use for a disease related to the liver, the lung, the kidney or the spleen.
(27) A therapeutic agent for a disease related to the liver, the lung, the kidney or the spleen, comprising the compound according to any one of the above described (1) to (10) or a pharmaceutically acceptable salt thereof, and a nucleic acid.
(28) A therapeutic agent for a disease related to the liver, the lung, the kidney or the spleen, comprising the composition according to any one of the above described (11) to (16).
(29) The therapeutic agent according to the above described (27) or (28), wherein the therapeutic agent is for intravenous administration.

Advantage of Invention

According to the present invention, a novel compound usable as a cationic lipid that facilitates introduction of a nucleic acid, for example, into a cell, and a composition or the like containing the novel compound can be provided.

BRIEF DESCRIPTION OF THE DRAWINGS

FIG. 1 shows the concentration of factor VII protein in plasma 48 hours after administration of each of preparations obtained in Examples 7 and 8, and preparations obtained in Comparative Examples 1 and 2 (preparations obtained by using compounds 2, 3, A and B, respectively) in amounts corresponding to 0.3 mg/kg and 0.03 mg/kg of siRNA to mice. The ordinate depicts the relative value of the concentration of factor VII protein in plasma with that in a physiological saline administration group defined as 1. The abscissa depicts compound No.

MODE FOR CARRYING OUT THE INVENTION

A compound of the present invention is a compound represented by formula (I):

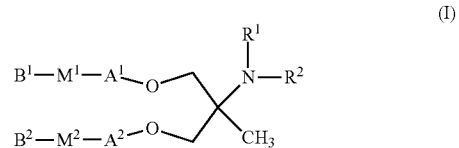

wherein $R^1$ and $R^2$ are, the same or different, a hydrogen atom or C1-C3 alkyl;
$A^1$ and $A^2$ are, the same or different, linear or branched C8-C20 alkylene or C8-C20 alkenylene;
$M^1$ and $M^2$ are, the same or different, selected from the group consisting of —C=C—, —OC(O)—, —C(O)O—, —SC(O)—, —C(O)S—, —OC(S)—, —C(S)O—, —SS—, —C($R^5$)=N—, —N=C($R^5$)—, —C($R^5$)=N—O—, —O—N=C($R^5$)—, —N($R^5$)C(O)—, —C(O)N($R^5$)—, —N($R^5$)C(S)—, —C(S)N($R^5$)—, —N($R^5$)C(O)N($R^6$)—, —N($R^5$)C(O)O—, —OC(O)N($R^5$)—, and —OC(O)O—;
$R^5$ and $R^6$ are, the same or different, a hydrogen atom or C1-C3 alkyl; and
$B^1$ and $B^2$ are, the same or different, linear or branched C1-C16 alkyl or C2-C16 alkenyl.

The compound represented by formula (I) has a lipophilic region containing two hydrocarbon groups and a hydrophilic region containing one positively charged polar head group, and has properties of a cationic lipid.

The compound represented by formula (I) is sometimes referred to as the compound (I) below. The same holds true for compounds of other formula numbers.

Examples of the C1-C3 alkyl include methyl, ethyl, propyl, isopropyl, cyclopropyl or the like.

Examples of the linear or branched C8-C20 alkylene include octylene, nonylene, decylene, undecylene, tridecylene, tetradecylene, 2,6,10-trimethylundecylene, pentadecylene, 3,7,11-trimethyldodecylene, hexadecylene, heptadecylene, octadecylene, nonadecylene, 2,6,10,14-tetramethylpentadecylene, 3,7,11,15-tetramethylhexadecylene, or the like.

Regarding the linear or branched C8-C20 alkylene, for example, in 2,6,10-trimethylundecylene, 2,6,10-corresponding to the substitution position of the substituent is indicated assuming that a carbon atom is in position 1 in $A^1$ and $A^2$ bonded to an oxygen atom in $-A^1-O—$ or $-A^2-O—$.

The linear or branched C8-C20 alkenylene can be any linear or branched C8-C20 alkylene group having one or more double bonds, and examples include (Z)-tetradec-9-enylene, (Z)-hexadec-9-enylene, (Z)-octadec-6-enylene, (Z)-octadec-9-enylene, (E)-octadec-9-enylene, (Z)-octadec-11-enylene, (9Z,12Z)-octadeca-9,12-dienylene, (9Z,12Z,15Z)-octadeca-9,12,15-trienylene, or the like.

Regarding the linear or branched C8-C20 alkenylene, for example, in (Z)-tetradec-9-enylene, -9- corresponding to the position of the double bond is indicated assuming that a carbon atom is in position 1 in $A^1$ and $A^2$ bonded to an oxygen atom in $-A^1-O—$ or $-A^2-O—$.

Examples of the linear or branched C1-C16 alkyl include methyl, ethyl, propyl, isopropyl, butyl, tert-butyl, hexyl, octyl, nonyl, decyl, dodecyl, tridecyl, tetradecyl, 3,7,11-trimethyldodecyl, hexadecyl, or the like.

Regarding the linear or branched C1-C16 alkyl, for example, in 3,7,11-trimethyldodecyl, 3,7,11-corresponding to the substitution position of the substituent is indicated assuming that a carbon atom is in position 1 in $B^1$ and $B^2$ bonded to $M^1$ and $M^2$.

The linear or branched C2-C16 alkenyl can be any linear or branched C2-C16 alkyl having one or more double bonds among linear or branched C1-C16 alkyls, and examples include (Z)-but-2-ene, (Z)-pent-2-ene, (Z)-hex-2-ene, (Z)-hept-2-ene, (Z)-oct-2-ene, (Z)-non-2-ene, (Z)-non-3-ene, (E)-non-2-ene, non-8-ene, (Z)-dodec-2-ene, (Z)-dodec-2-ene, (Z)-tridec-2-ene, or the like.

Regarding the linear or branched C2-C16 alkenyl, for example, in (Z)-but-2-ene, -2- corresponding to the substitution position of the substituent is indicated assuming that a carbon atom is in position 1 in $B^1$ and $B^2$ bonded to $M^1$ and $M^2$.

In the present invention, a group having a cyclopropane ring formed by adding formally a methylene biradical to a double bond of the linear or branched C8-C20 alkenylene is also included in the linear or branched C8-C20 alkenylene. The same holds true for the linear or branched C2-C16 alkenyl and a case where $M^1$ and $M^2$ are $—C=C—$ (double bond).

For example, in (Z)-non-2-ene, the following group having a cyclopropane ring is also included in the linear or branched C8-C20 alkenylene of the present invention.

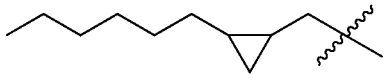 [SMILES: *CC1CC1CCCCCC]

$R^1$ and $R^2$ are, the same or different, a hydrogen atom or C1-C3 alkyl.

$R^1$ and $R^2$ are, the same or different, preferably a hydrogen atom, methyl, ethyl or propyl, and more preferably a hydrogen atom or methyl.

A combination of ($R^1$, $R^2$) is preferably (hydrogen atom, hydrogen atom), (hydrogen atom, methyl) or (methyl, methyl), and more preferably (hydrogen atom, methyl) or (methyl, methyl).

$A^1$ and $A^2$ are, the same or different, linear or branched C8-C20 alkylene or C8-C20 alkenylene.

$A^1$ and $A^2$ are, the same or different, when they are alkylene, preferably linear C8-C20 alkylene, and more preferably linear C8-C12 alkylene.

$A^1$ and $A^2$ are, the same or different, preferably octylene, nonylene, undecylene, tridecylene or pentadecylene, and more preferably octylene, nonylene or undecylene.

$A^1$ and $A^2$ are, the same or different, when they are alkenylene, preferably linear C8-C20 alkenylene, and more preferably linear C10-C14 alkenylene.

$A^1$ and $A^2$ are, the same or different, preferably (Z)-undec-9-enylene, (Z)-tridec-11-enylene, (Z)-tetradec-9-enylene, (Z)-hexadec-9-enylene, (Z)-octadec-9-enylene, (Z)-octadec-11-enylene, or (9Z,12Z)-octadeca-9,12-dienylene.

$A^1$ and $A^2$ are preferably the same.

$M^1$ and $M^2$ are, the same or different, $—C=C—$, $—OC(O)—$, $—C(O)O—$, $—SC(O)—$, $—C(O)S—$, $—OC(S)—$, $—C(S)O—$, $—SS—$, $—C(R^5)=N—$, $—N=C(R^5)—$, $—C(R^5)=N—O—$, $—O—N=C(R^5)—$, $—N(R^5)C(O)—$, $—C(O)N(R^5)—$, $—N(R^5)C(S)—$, $—C(S)N(R^5)—$, $—N(R^5)C(O)N(R^6)—$, $—N(R^5)C(O)O—$, $—OC(O)N(R^5)—$ or $—OC(O)O—$.

$M^1$ and $M^2$ are, the same or different, preferably $—C=C—$, $—OC(O)—$, $—C(O)O—$, $—C(O)(NR^5)—$, $—N(R^5)C(O)—$, $—N(R^5)C(O)—$, $—N(R^5)C(O)N(R^6)—$, $—N(R^5)C(O)O—$, $—OC(O)N(R^5)—$ or $—OC(O)O—$, and more preferably $—C=C—$, $—OC(O)—$, or $—C(O)O—$.

Regarding a bond of each structure of $M^1$ and $M^2$, for example, $—OC(O)—$ means a structure of $B^1—OC(O)-A^1$. $M^1$ and $M^2$ are preferably the same.

$R^5$ and $R^6$ in $M^1$ and $M^2$ are, the same or different, a hydrogen atom or C1-C3 alkyl.

$R^5$ and $R^6$ are, the same or different, preferably a hydrogen atom, methyl, ethyl or propyl, more preferably a hydrogen atom or methyl, and further preferably a hydrogen atom.

$B^1$ and $B^2$ are, the same or different, linear or branched C1-C16 alkyl or C2-C16 alkenyl.

$B^1$ and $B^2$ are, the same or different, when they are alkyl, preferably linear C1-C16 alkyl, and more preferably linear C2-C9 alkyl.

$B^1$ and $B^2$ are, the same or different, preferably pentyl, octyl, nonyl, decyl or dodecyl.

$B^1$ and $B^2$ are, the same or different, when they are alkenyl, preferably linear C2-C16 alkenyl, and more preferably linear C3-C9 alkenyl.

$B^1$ and $B^2$ are, the same or different, preferably (Z)-hept-2-ene, (Z)-oct-2-ene, (Z)-non-2-ene, (Z)-non-3-ene, non-8-ene, (Z)-dodec-2-ene or (Z)-tridec-2-ene. $B^1$ and $B^2$ are preferably the same.

$B^1-M^1-A^1$ and $B^2-M^2-A^2$ are the same or different, and $B^1$ and $B^2$, $M^1$ and $M^2$, and $A^1$ and $A^2$ can be any combinations selected from the structures described with respect to these groups.

$B^1-M^1-A^1$ and $B^2-M^2-A^2$ are preferably the same.

$B^1-M^1-A^1$ and $B^2-M^2-A^2$ are, the same or different, preferably selected from the group consisting of (Z)-tetradec-9-enyl, (Z)-hexadec-9-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, and (Z)-docos-13-enyl, and more preferably selected from the group consisting of (Z)-hexadec-9-enyl, (Z)-octadec-9-enyl, (9Z,12Z)-octadeca-9,12-dienyl, and (11Z,14Z)-icosa-11,14-dienyl.

$B^1-M^1-A^1$ and $B^2-M^2-A^2$ are, the same or different, preferably any of the following structures (1) to (5), more preferably, the same, any of the following structures (1) to (5), and further preferably, the same, any of the following structures (1) and (4):

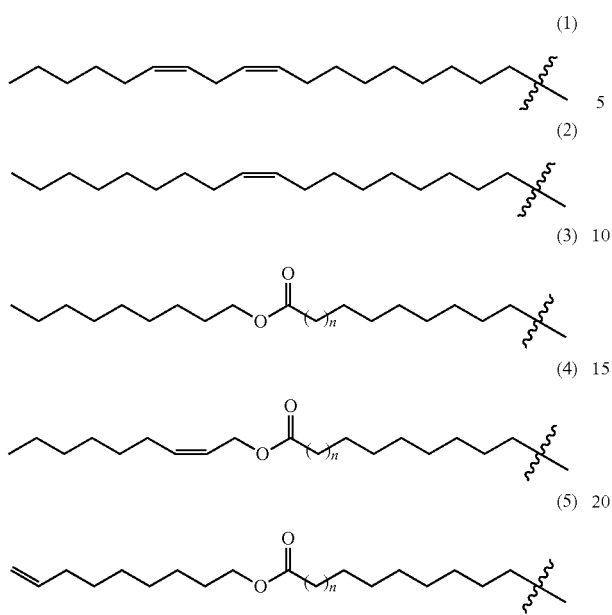

wherein n is an integer from 1 to 4.

Methods for producing the compound of the present invention will be described. In the production methods shown below, if defined groups react under conditions of the production methods or are unsuitable for carrying out the production methods, the desired compounds can be produced by use of introduction and removal methods of protective groups commonly used in organic synthetic chemistry [e.g., methods described in Protective Groups in Organic Synthesis, third edition, T. W. Greene, John Wiley & Sons Inc. (1999) or the like] or the like. If necessary, the order of reaction steps including substituent introduction or the like may be changed.

Production Method 1

Compounds (I) wherein both of $R^1$ and $R^2$ are hydrogen atoms, that is, compound (Ia), and wherein $R^1$ and $R^2$ are the same, that is, compound (Ib), can be produced by the following method:

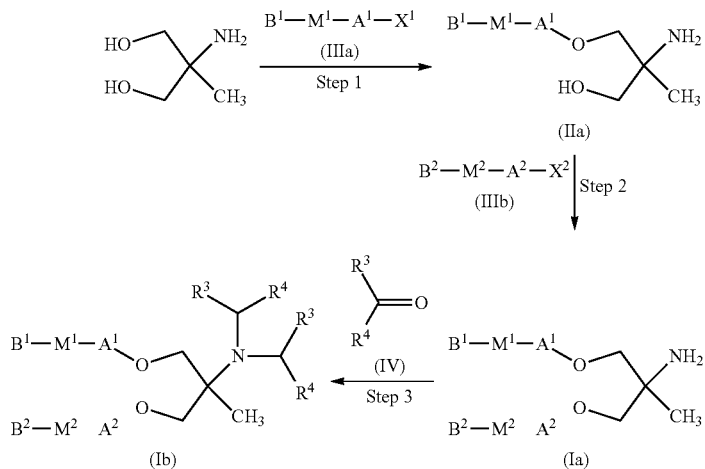

wherein $A^1$, $A^2$, $B^1$, $B^2$, $M^1$ and $M^2$ are each as defined above, $X^1$ and $X^2$ are, the same or different, a leaving group such as a chlorine atom, a bromine atom, an iodine atom, trifluoromethanesulfonyloxy, methanesulfonyloxy, benzenesulfonyloxy, or p-toluenesulfonyloxy, $R^3$ is a hydrogen atom, methyl or ethyl, $R^4$ is a hydrogen atom or methyl, or $R^3$ and $R^4$ form a cyclopropyl ring together with an adjacent carbon atom (provided that $R^4$ is not methyl when $R^3$ is a hydrogen atom or ethyl).

Step 1 and Step 2

Compound (IIa) can be produced by reacting compound (IIIa) with 2-amino-2-methyl-1,3-propanediol at a temperature between room temperature and 200° C. for 5 minutes to 100 hours in the presence of 1 to 10 equivalents of a base without a solvent or in a solvent. Further, compound (Ia) can be produced by reacting compound (IIa) with compound (IIIb) at a temperature between room temperature and 200° C. for 5 minutes to 100 hours in the presence of 1 to 10 equivalents of a base without a solvent or in a solvent.

Examples of the solvent include dichloromethane, 1,2-dichloroethane, toluene, diethyl ether, tetrahydrofuran, 1,2-dimethoxyethane, 1,4-dioxane, pyridine or the like, and these solvents can be used singly or as a mixture.

Examples of the base include sodium methoxide, potassium tert-butoxide, sodium hydride, lithium diisopropylamide, lithium hexamethyldisilazane, sodium hexamethyldisilazane, n-butyllithium, or the like.

Compound (IIIa) and compound (IIIb) can each be obtained as a commercially available product or by a method known in the art (e.g., "The Fifth Series of Experimental Chemistry 13, Synthesis of Organic Compound I", 5th edition, p. 374, Maruzen Co., Ltd. (2005)) or a method equivalent thereto.

When $B^1$-$M^1$-$A^1$ and $B^2$-$M^2$-$A^2$ are the same, compound (Ia) can be obtained by using 2 equivalents or more of compound (IIIa) in step 1.

2-amino-2-methyl-1,3-propanediol can be obtained as a commercially available product.

Step 3

Compound (Ib) can be produced by reacting compound (Ia), with 2 to 20 equivalents of compound (IV), at a temperature between −20° C. and 150° C. for 5 minutes to 72 hours in the presence of preferably 1 equivalent to a large excess of a reducing agent and, if necessary, preferably 1 to 10 equivalents of an acid, in a solvent.

Examples of the solvent include methanol, ethanol, tert-butyl alcohol, dichloromethane, chloroform, 1,2-dichloroethane, toluene, ethyl acetate, acetonitrile, diethyl ether, tetrahydrofuran, 1,2-dimethoxyethane, 1,4-dioxane, N,N-dimethylformamide, N,N-dimethylacetamide, N-methylpyrrolidone, water, or the like. These solvents are used singly or as a mixture.

Examples of the reducing agent include sodium triacetoxyborohydride, sodium cyanoborohydride, or the like.

Examples of the acid include hydrochloric acid, acetic acid, or the like.

Compound (IV) can be obtained as a commercially available product.

Production Method 2

Compounds (I) wherein $R^1$ and $R^2$ are different, that is, compounds (Ic) and (Id), can be produced by the following method:

Examples of the base include sodium methoxide, potassium tert-butoxide, sodium hydride, lithium diisopropylamide, lithium hexamethyldisilazane, sodium hexamethyldisilazane, n-butyllithium, potassium carbonate, cesium carbonate, triethylamine, or the like.

Compound (IIIc) can be obtained as a commercially available product.

Step 6

Compound (Ic) is obtained by removing the protective group PG on compound (IIc) by an appropriate method. Methods for removing protective groups commonly used in organic synthetic chemistry [e.g., removal methods described in Protective Groups in Organic Synthesis, third edition, T. W. Greene, John Wiley & Sons Inc. (1999) or the

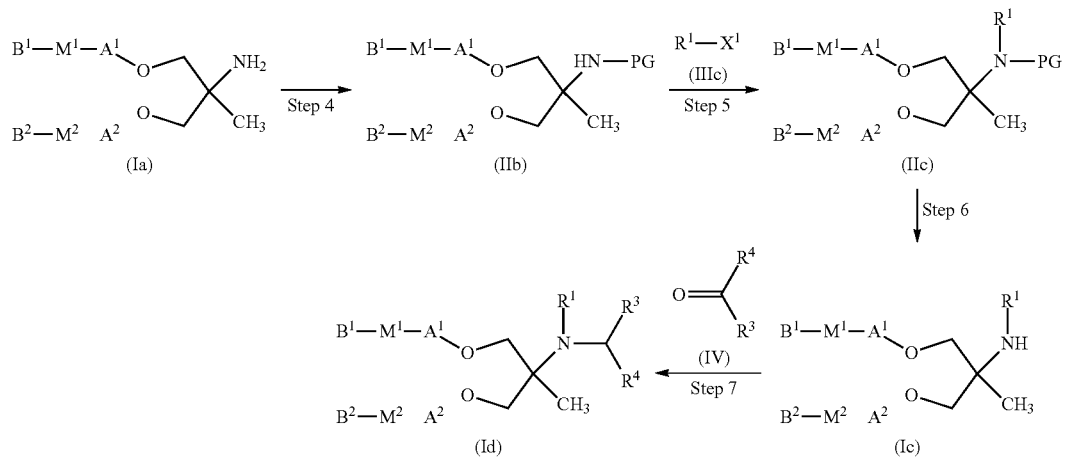

wherein $A^1$, $A^2$, $B^1$, $B^2$, $M^1$, $M^2$, $R^1$, $R^3$, $R^4$ and $X^1$ are each as defined above, and PG is a protective group.

Step 4

Compound (IIb) can be produced by protecting compound (Ia) by a protective group commonly used in organic synthetic chemistry [e.g., protective groups described in Protective Groups in Organic Synthesis, third edition, T. W. Greene, John Wiley & Sons Inc. (1999)].

Step 5

Compound (IIc) can be produced by reacting compound (IIb) with compound (IIIc) at a temperature between −20° C. and 150° C. for 5 minutes to 72 hours in the presence of 1 to 10 equivalents of a base without a solvent or in a solvent.

Examples of the solvent include dichloromethane, 1,2-dichloroethane, toluene, diethyl ether, tetrahydrofuran, 1,2-dimethoxyethane, 1,4-dioxane, pyridine, N,N-dimethylformamide, N,N-dimethylacetamide, or the like, and these solvents can be used singly or as a mixture.

like] can be used as the protective group removal method. The compound of interest can thereby be produced.

Step 7

Compound (Id) can be produced by reacting compound (Ic) with 1 to 10 equivalents of compound (IV) at a temperature between −20° C. and 150° C. for 5 minutes to 72 hours in the presence of preferably 1 equivalent to a large excess of a reducing agent and, if necessary, preferably 1 to 10 equivalents of an acid in a solvent.

Examples of the solvent, the reducing agent and the acid include those listed in step 3.

Production Method 3

Compounds (I) wherein $M^1$ and $M^2$ are respectively —OC(O)—, that is, compounds (Ic') and (Id'), can be produced also by the following method:

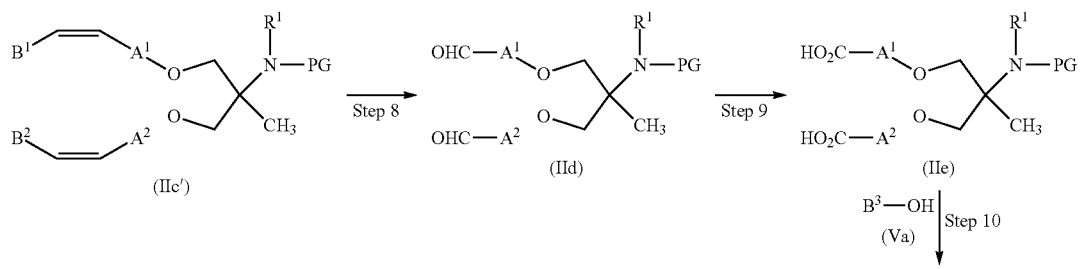

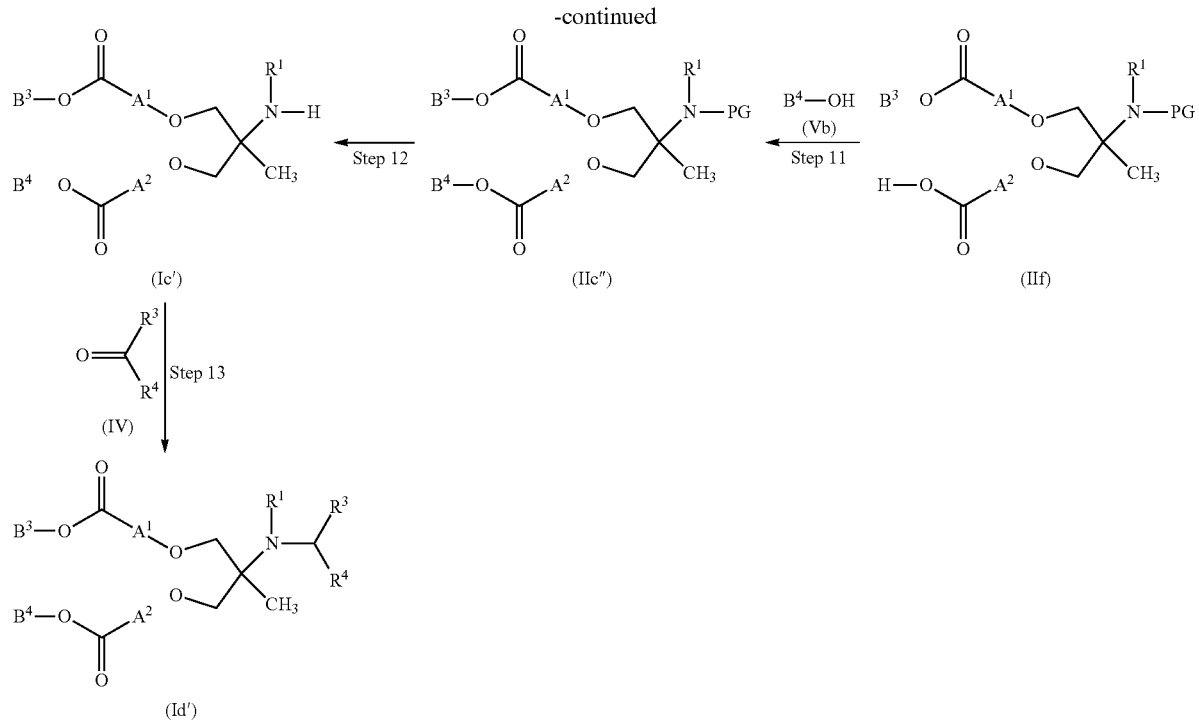

wherein $A^1$, $A^2$, $B^1$, $B^2$, $R^1$, $R^3$, $R^4$ and PG are each as defined above, and $B^3$ and $B^4$ are linear or branched C1-C16 alkyl or C2-C16 alkenyl.

Step 8

Compound (Id) can be produced by reacting compound (IIc') with an oxidizing agent at a temperature between −20° C. and 150° C. for 5 minutes to 72 hours in a solvent.

Examples of the oxidizing agent include ozone, osmium tetroxide/sodium periodate, osmium tetroxide/lead tetraacetate, or the like.

Examples of the solvent include those listed in step 3.

Compound (IIc') can be produced by the method described in Production Method 2.

Step 9

Compound (IIe) can be produced by reacting compound (IId) with an oxidizing agent at a temperature between −20° C. and 150° C. for 5 minutes to 72 hours in a solvent.

Examples of the oxidizing agent include Jones reagent, pyridinium dichromate, ruthenium tetroxide, sodium chlorite, or the like.

Examples of the solvent include tert-butyl alcohol, dichloromethane, chloroform, 1,2-dichloroethane, toluene, ethyl acetate, acetone, acetonitrile, diethyl ether, tetrahydrofuran, 1,2-dimethoxyethane, 1,4-dioxane, N,N-dimethylformamide, N,N-dimethylacetamide, N-methyl pyrrolidone, water, or the like, and these solvents can be used singly or as a mixture.

Step 10 and Step 11

Compound (IIf) can be produced by reacting compound (IIe) and compound (Va) at a temperature between room temperature and 200° C. for 5 minutes to 100 hours in the presence of 1 to 10 equivalents of a condensing agent and 1 to 10 equivalents of a base without a solvent or in a solvent. Besides, compound (IIc") can be produced by reacting compound (IIf) and compound (Vb) at a temperature between room temperature and 200° C. for 5 minutes to 100 hours in the presence of 1 to 10 equivalents of a condensing agent and 1 to 10 equivalents of a base without a solvent or in a solvent.

Examples of the solvent include dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methyl pyrrolidone, pyridine, or the like, and these solvents can be used singly or as a mixture.

Examples of the condensing agent include 1-ethyl-3-(3-dimethylaminopropyl)carbodiimide hydrochloride, N,N'-dicyclohexylcarbodiimide, 4-(4,6-dimethoxy-1,3,5-triazin-2-yl)-4-methylmorpholinium chloride n hydrate, 1H-benzotriazol-1-yloxytris(dimethylamino)phosphonium hexafluorophosphate, 0-(7-azabenzotriazol-1-yl)-N,N,N',N'-tetramethyluronium hexafluorophosphate, or the like.

Examples of the base include potassium carbonate, cesium carbonate, triethylamine, N,N-diisopropylethylamine, N-methylmorpholine, pyridine, or the like.

Compound (Va) and compound (Vb) can be obtained as commercially available products.

Compound (IIc") wherein $B^3$ and $B^4$ are the same can be obtained by using 2 or more equivalents of compound (Va) in step 10.

Step 12

Compound (Ic') is obtained by removing the protective group PG on compound (IIc") by appropriate methods. Methods for removing protective groups commonly used in organic synthetic chemistry [e.g., removal methods described in Protective Groups in Organic Synthesis, third edition, T. W. Greene, John Wiley & Sons Inc. (1999) or the like] can be used as the protective group removal methods, and thus, the compound of interest can be produced.

Step 13

Compound (Id') can be produced by reacting compound (Ic') with 1 to 10 equivalents of compound (IV) at a temperature between −20° C. and 150° C. for 5 minutes to 72 hours in the presence of preferably 1 equivalent to a large excess of a reducing agent and, if necessary, preferably 1 to 10 equivalents of an acid in a solvent.

Examples of the solvent and the acid include those listed in step 3.

Among compounds (I), compounds other than compounds (Ia) to (Id) described above can be produced according to the production methods described above or by the application of general production methods commonly used in organic synthetic chemistry, by adopting starting materials, reagents, or the like suitable for the structures of the compounds of interest.

The intermediates and the desired compounds in the production methods described above can each be isolated and purified by separation and purification methods commonly used in organic synthetic chemistry, for example, filtration, extraction, washing, drying, concentration, recrystallization, various chromatography techniques, or the like. Alternatively, each intermediate may be subjected to the next reaction without being particularly purified.

In the compound of the present invention, hydrogen ions may be coordinated to a lone pair of electrons on the nitrogen atom in the structure, and in this case, the compound of the present invention may form a pharmaceutically acceptable salt with a pharmaceutically acceptable anion (as defined above), and the compound of the present invention also encompasses such a cationic lipid in which hydrogen ions are coordinated to a lone pair of electrons on the nitrogen atom.

In the present invention, examples of the pharmaceutically acceptable anion include: inorganic ions such as chloride ions, bromide ions, nitrate ions, sulfate ions and phosphate ions; and organic acid ions such as acetate ions, oxalate ions, maleate ions, fumarate ions, citrate ions, benzoate ions, and methanesulfonate ions, or the like.

Some compounds of the present invention may have stereoisomers such as geometric isomers and optical isomers, tautomers, or the like. The compounds of the present invention encompass all possible isomers including them, and mixtures thereof.

Some or all of the atoms in the compounds of the present invention may be replaced with their corresponding isotopic atoms. Compound (I) also encompasses such a compound containing isotopic atoms replaced therefor. For example, some or all of the hydrogen atoms in compound (I) may each be a hydrogen atom having an atomic weight of 2 (deuterium atom).

The compound derived from the compounds of the present invention by the replacement of some or all of the atoms with their corresponding isotopic atoms can be produced in the same way as in each production method described above by using commercially available building blocks. The compound derived from compound (I) by the replacement of some or all of the hydrogen atoms with deuterium atoms can also be synthesized by use of, for example, a method which involves deuterating an alcohol, a carboxylic acid, or the like using an iridium complex as a catalyst and heavy water as a deuterium source [see J. Am. Chem. Soc., Vol. 124, No. 10, 2092 (2002) or the like].

Concrete examples of the compounds of the present invention are shown in Table 1. However, the compound of the present invention is not intended to be limited to them.

TABLE 1

| Compound No. | Structure |
| --- | --- |
| 1 | 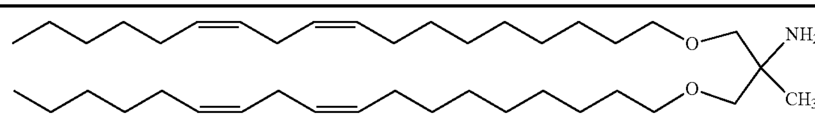 |
| 2 | 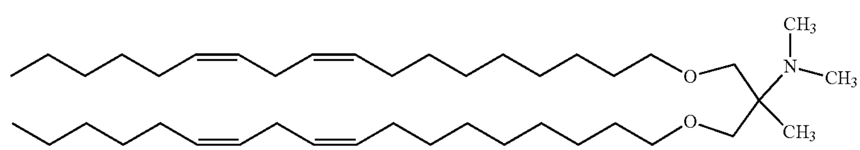 [SMILES: CCCCC/C=C\C/C=C\CCCCCCCCOCC(C)(COCCCCCCCC/C=C\C/C=C\CCCCC)N(C)C] |
| 3 | 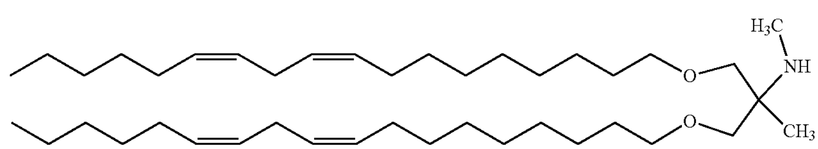 [SMILES: CCCCC/C=C\C/C=C\CCCCCCCCOCC(C)(COCCCCCCCC/C=C\C/C=C\CCCCC)NC] |
| 4 | 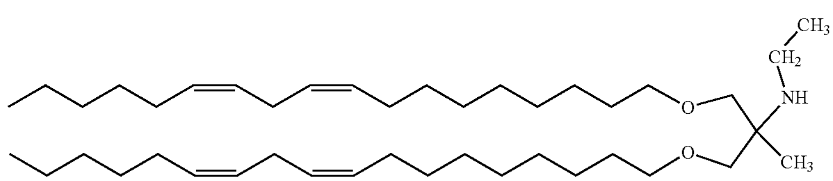 [SMILES: CCCCC/C=C\C/C=C\CCCCCCCCOCC(C)(COCCCCCCCC/C=C\C/C=C\CCCCC)NCC] |
| 5 | 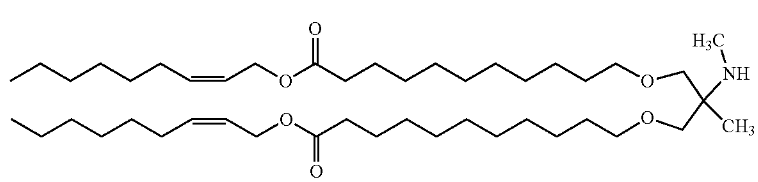 [SMILES: CCCCCC/C=C\COC(=O)CCCCCCCCCCOCC(C)(COCCCCCCCCCCC(=O)OC/C=C\CCCCCC)NC] |

TABLE 1-continued

| Compound No. | Structure |
| --- | --- |
| 6 | (chemical structure) |

The nucleic acid used in the present invention can be any molecule as long as the molecule is obtained by the polymerization of, for example, nucleotides and/or molecules having functions equivalent to nucleotides. Examples thereof include ribonucleic acid (RNA) which is a polymer of ribonucleotides, deoxyribonucleic acid (DNA) which is a polymer of deoxyribonucleotides, chimeric nucleic acids consisting of RNA and DNA, and nucleotide polymers derived from these nucleic acids by the replacement of at least one nucleotide with a molecule having a function equivalent to the nucleotide or the like. A derivative at least partially containing the structure of the molecule obtained by the polymerization of nucleotides and/or molecules having functions equivalent to nucleotides is also included in the nucleic acid of the present invention. In the present invention, uracil U and thymine T can be used interchangeably with each other.

Examples of the molecules having functions equivalent to nucleotides include nucleotide derivatives or the like.

The nucleotide derivative can be any molecule as long as the molecule is, for example, a modified nucleotide. For example, a modified ribonucleotide or deoxyribonucleotide molecule is suitably used for improving nuclease resistance or stabilizing the molecule against the other decomposition factors, for enhancing affinity for a complementary strand nucleic acid, for enhancing cell permeability, or for visualizing the molecule, as compared with RNA or DNA.

Examples of the nucleotide derivative include nucleotides modified at the sugar moiety, nucleotides modified at the phosphodiester bond, nucleotides modified at the base, or the like.

The nucleotide modified at the sugar moiety can be, for example, any nucleotide in which a part or the whole of the chemical structure of its sugar is modified or substituted with an arbitrary substituent or substituted with an arbitrary atom. A 2'-modified nucleotide is preferably used.

Examples of the modifying group in the nucleotide modified at the sugar moiety include 2'-cyano, 2'-alkyl, 2'-substituted alkyl, 2'-alkenyl, 2'-substituted alkenyl, 2'-halogen, 2'-O-cyano, 2'-O-alkyl, 2'-O-substituted alkyl, 2'-O-alkenyl, 2'-O-substituted alkenyl, 2'-S-alkyl, 2'-S-substituted alkyl, 2'-S-alkenyl, 2'-S-substituted alkenyl, 2'-amino, 2'-NH-alkyl, 2'-NH-substituted alkyl, 2'-NH-alkenyl, 2'-NH-substituted alkenyl, 2'-SO-alkyl, 2'-SO-substituted alkyl, 2'-carboxy, 2'-CO-alkyl, 2'-CO-substituted alkyl, 2'-Se-alkyl, 2'-Se-substituted alkyl, 2'-SiH$_2$-alkyl, 2'-SiH$_2$-substituted alkyl, 2'-ONO$_2$, 2'-NO$_2$, 2'-N$_3$, 2'-amino acid residues (which results from the removal of a hydroxy group from the carboxylic acids of amino acids), 2'-O-amino acid residues (as defined in the amino acid residues), or the like.

Examples of the nucleotide modified at the sugar moiety include bridged nucleic acid (BNA) having two cyclic structures by the introduction of a bridged structure to the sugar moiety and specifically include locked nucleic acid (LNA) having the oxygen atom at position 2' and the carbon atom at position 4' bridged via methylene ["Tetrahedron Letters", Volume 38, Issue 50, 1997, Pages 8735-8738, and "Tetrahedron", Volume 54, Issue 14, 1998, Pages 3607-3630], ethylene bridged nucleic acid (ENA) ["Nucleic Acid Research", 32, e175 (2004)], or the like.

Further examples of the nucleotide modified at the sugar moiety also include peptide nucleic acid (PNA) [Acc. Chem. Res., 32, 624 (1999)], oxypeptide nucleic acid (OPNA) [J. Am. Chem. Soc., 123, 4653 (2001)], peptide ribonucleic acid (PRNA) [J. Am. Chem. Soc., 122, 6900 (2000)], or the like.

The modifying group in the nucleotide modified at the sugar moiety is preferably 2'-cyano, 2'-halogen, 2'-O-cyano, 2'-alkyl, 2'-substituted alkyl, 2'-O-alkyl, 2'-0-substituted alkyl, 2'-O-alkenyl, 2'-O-substituted alkenyl, 2'-Se-alkyl, 2'-Se-substituted alkyl, or the like, more preferably 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O-[2-(methoxy)ethyl], 2'-O-(3-aminopropyl), 2'-O-[2-(N,N-dimethylaminooxy)ethyl], 2'-O-[3-(N,N-dimethylamino)propyl], 2'-O-{2-[2-(N,N-dimethylamino)ethoxy]ethyl}, 2'-O-[2-(methylamino)-2-oxoethyl], 2'-Se-methyl, or the like, further preferably 2'-methyl, 2'-O-ethyl, 2'-fluoro, or the like, most preferably 2'-O-methyl and 2'-O-ethyl.

Further, the modifying group in the nucleotide modified at the sugar moiety can also be defined from its size, preferably the modifying group corresponds to a size from fluoro to —O-butyl, and more preferably the modifying group corresponds to a size from —O-methyl to —O-ethyl.

Examples of the alkyl in the modifying group in the nucleotide modified at the sugar moiety include alkyl having 1 to 6 carbon atoms. The alkyl having 1 to 6 carbon atoms is, for example, methyl, ethyl, propyl, isopropyl, butyl, isobutyl, sec-butyl, tert-butyl, pentyl, isopentyl, neopentyl, hexyl or the like.

Examples of the alkenyl in the modifying group in the nucleotide modified at the sugar moiety include alkenyl having 3 to 6 carbon atoms. Examples thereof include allyl, 1-propenyl, butenyl, pentenyl, hexenyl, or the like.

Examples of the halogen in the modifying group in the nucleotide modified at the sugar moiety include a fluorine atom, a chlorine atom, a bromine atom, an iodine atom, or the like.

Examples of the amino acid in the amino acid residue include aliphatic amino acids (specifically, glycine, alanine, valine, leucine, isoleucine, etc.), hydroxyamino acids (specifically, serine, threonine, etc.), acidic amino acids (specifically, aspartic acid, glutamic acid, etc.), acidic amino acid amides (specifically, asparagine, glutamine, etc.), basic amino acids (specifically, lysine, hydroxylysine, arginine, ornithine, etc.), sulfur-containing amino acids (specifically, cysteine, cystine, methionine, etc.), imino acids (specifically, proline, 4-hydroxyproline etc.), or the like.

Examples of the substituent in the substituted alkyl or the substituted alkenyl in the modifying group in the nucleotide modified at the sugar moiety include halogen (as defined above), hydroxy, sulfanyl, amino, oxo, —O-alkyl (the alkyl moiety of the —O-alkyl is as defined in the above-described alkyl having 1 to 6 carbon atoms), —S-alkyl (the alkyl moiety of the —S-alkyl is as defined in the above-described alkyl having 1 to 6 carbon atoms), —NH-alkyl (the alkyl moiety of the —NH-alkyl is as defined in the above-described alkyl having 1 to 6 carbon atoms), dialkylaminooxy (the two alkyl moieties of the dialkylaminooxy are, the same or different, as defined in the above-described alkyl having 1 to 6 carbon atoms), dialkylamino (the two alkyl moieties of the dialkylamino are, the same or different, as defined in the above-described alkyl having 1 to 6 carbon atoms), dialkylaminoalkyloxy (the two alkyl moieties of the dialkylaminoalkyloxy are, the same or different, as defined in the above-described alkyl having 1 to 6 carbon atoms, and the alkylene moiety means a moiety obtained by removal of one hydrogen atom from the alkyl), or the like. The number of substituents is preferably 1 to 3.

The nucleotide modified at the phosphodiester bond can be any nucleotide in which a part or the whole of the chemical structure of its phosphodiester bond is modified or substituted with an arbitrary substituent or substituted with an arbitrary atom. Examples thereof include a nucleotide resulting from the substitution of the phosphodiester bond with a phosphorothioate bond, a nucleotide resulting from the substitution of the phosphodiester bond with a phosphorodithioate bond, a nucleotide resulting from the substitution of the phosphodiester bond with an alkyl phosphonate bond, a nucleotide resulting from the substitution of the phosphodiester bond with a phosphoramidate bond, or the like.

The nucleotide modified at the base can be any nucleotide in which a part or the whole of the chemical structure of its base is modified or substituted with an arbitrary substituent or substituted with an arbitrary atom. Examples thereof include a nucleotide resulting from the substitution of an oxygen atom in the base with a sulfur atom, a nucleotide resulting from the substitution of a hydrogen atom with an alkyl group having 1 to 6 carbon atoms, a nucleotide resulting from the substitution of a methyl group with a hydrogen atom or an alkyl group having 2 to 6 carbon atoms, a nucleotide resulting from the protection of an amino group with a protective group such as an alkyl group having 1 to 6 carbon atoms or an alkanoyl group having 1 to 6 carbon atoms, or the like.

Further examples of the nucleotide derivative include nucleotide derivatives that are modified nucleotides or each have at least one modified sugar moiety, phosphodiester bond or base, and contain an additional chemical substance, such as lipid, phospholipid, phenazine, folate, phenanthridine, anthraquinone, acridine, fluorescein, rhodamine, coumarin, or dye, added thereto, and specifically include 5'-polyamine-added nucleotide derivatives, cholesterol-added nucleotide derivatives, steroid-added nucleotide derivatives, bile acid-added nucleotide derivatives, vitamin-added nucleotide derivatives, green fluorescent dye (Cy3)-added nucleotide derivatives, red fluorescent dye (Cy5)-added nucleotide derivatives, fluorescein (6-FAM)-added nucleotide derivatives, biotin-added nucleotide derivatives, or the like.

In the nucleic acid used in the present invention, the nucleotide or the nucleotide derivative may form a bridged structure, such as an alkylene structure, a peptide structure, a nucleotide structure, an ether structure, an ester structure, and a structure combined with at least one of these structures, with another nucleotide or nucleotide derivative within the nucleic acid.

Examples of the nucleic acid used in the present invention preferably include nucleic acids silencing a target gene and more preferably include nucleic acids having a silencing effect on a target gene through the use of RNA interference (RNAi).

The target gene in the present invention is not particularly limited as long as the gene is expressed by producing mRNA. For example, a gene related to tumor or inflammation is preferred. Examples thereof include genes encoding proteins such as vascular endothelial growth factor (hereinafter, abbreviated to VEGF), vascular endothelial growth factor receptor (hereinafter, abbreviated to VEGFR), fibroblast growth factor, fibroblast growth factor receptor, platelet-derived growth factor, platelet-derived growth factor receptor, hepatocyte growth factor, hepatocyte growth factor receptor, Kruppel-like factor (hereinafter, abbreviated to KLF), expressed sequence tag (Ets) transcription factor, nuclear factor, hypoxia-inducible factor, cell cycle-related factor, chromosomal replication-related factor, chromosomal repair-related factor, microtubule-related factor, growth signal pathway-related factor, growth-related transcription factor, and apoptosis-related factor, or the like, and specifically include VEGF gene, VEGFR gene, fibroblast growth factor gene, fibroblast growth factor receptor gene, platelet-derived growth factor gene, platelet-derived growth factor receptor gene, hepatocyte growth factor gene, hepatocyte growth factor receptor gene, KLF gene, Ets transcription factor gene, nuclear factor gene, hypoxia-inducible factor gene, cell cycle-related factor gene, chromosomal replication-related factor gene, chromosomal repair-related factor gene, microtubule-related factor gene (e.g., CKAP5 gene or the like), growth signal pathway-related factor gene (e.g., KRAS gene or the like), growth-related transcription factor gene, apoptosis-related factor (e.g., BCL-2 gene or the like), or the like.

The target gene according to the present invention is preferably, for example, a gene expressed in the liver, the lung, the kidney, or the spleen. Examples thereof include the aforementioned genes related to tumor or inflammation, and genes encoding proteins such as hepatitis B virus genome, hepatitis C virus genome, apolipoprotein (APO), hydroxymethylglutaryl (HMG) CoA reductase, kexin type 9 serine protease (PCSK9), factor 12, glucagon receptor, glucocorticoid receptor, leukotriene receptor, thromboxane A2 receptor, histamine Hi receptor, carbonic anhydrase, angiotensin-converting enzyme, renin, p53, tyrosine phosphatase (PTP), sodium-dependent glucose transport carrier, tumor necrosis factor, interleukin, hepcidin, trans siren, antithrombin, protein C, and matriptase enzyme (e.g., TMPRSS6 gene or the like), or the like.

Any nucleic acid such as a double-stranded nucleic acid (e.g., siRNA (short interference RNA) and miRNA (micro RNA)) or a single-stranded nucleic acid (e.g., shRNA (short hairpin RNA) antisense nucleic acid and ribozyme) may be used as the nucleic acid silencing a target gene as long as the nucleic acid comprises a nucleotide sequence complementary to, for example, a partial nucleotide sequence of the mRNA of a gene (target gene) encoding a protein or the like and silences the target gene. A double-stranded nucleic acid is preferred.

The nucleic acid comprising a nucleotide sequence complementary to a partial nucleotide sequence of the mRNA of the target gene is referred to as an antisense nucleic acid. A nucleic acid comprising a nucleotide sequence complementary to the nucleotide sequence of the antisense nucleic acid is also referred to as a sense strand nucleic acid. The sense strand nucleic acid refers to a nucleic acid capable of forming a duplex formation moiety by pairing with the antisense nucleic acid, such as a nucleic acid itself consisting of the partial nucleotide sequence of the target gene.

The double-stranded nucleic acid refers to a nucleic acid having a duplex formation moiety composed of paired two strands. The duplex formation moiety refers to a part in which nucleotides constituting the double-stranded nucleic acid, or derivatives thereof have formed a duplex by constituting base pairs. The base pairs constituting the duplex formation moiety are usually 15 to 27 base pairs, preferably 15 to 25 base pairs, more preferably 15 to 23 base pairs, further preferably 15 to 21 base pairs, particularly preferably 15 to 19 base pairs.

For example, a nucleic acid consisting of a partial sequence of the mRNA of the target gene, or a nucleic acid derived from the nucleic acid by the substitution, deletion or addition of 1 to 3 bases, preferably 1 or 2 bases, more preferably 1 base, and having silencing activity against the target protein is suitably used as the antisense nucleic acid of the duplex formation moiety. Each single-stranded nucleic acid constituting the double-stranded nucleic acid usually consists of a sequence of 15 to 30 bases (nucleosides), preferably 15 to 29 bases, more preferably 15 to 27 bases, further preferably 15 to 25 bases, particularly preferably 17 to 23 bases, most preferably 19 to 21 bases.

Either of the antisense strand or the sense strand constituting the double-stranded nucleic acid, or both of these nucleic acids may have a non-duplex-forming additional nucleic acid on the 3' or 5' side subsequent to the duplex formation moiety. This non-duplex-forming moiety is also referred to as an overhang.

For example, a double-stranded nucleic acid having an overhang consisting of 1 to 4 bases, usually 1 to 3 bases, at the 3' end or the 5' end of at least one of the strands is used as the double-stranded nucleic acid having the overhang. A double-stranded nucleic acid having an overhang consisting of 2 bases is preferably used, and a double-stranded nucleic acid having an overhang consisting of dTdT or UU is more preferably used. The overhang can be located in only the antisense strand, only the sense strand, and both of the antisense strand and the sense strand. A double-stranded nucleic acid having overhangs in both of the antisense strand and the sense strand is preferably used.

A sequence partially or completely matching the nucleotide sequence of the mRNA of the target gene, or a sequence partially or completely matching the nucleotide sequence of a complementary strand of the mRNA of the target gene may be used subsequently to the duplex formation moiety. Alternatively, for example, a nucleic acid molecule that forms the double-stranded nucleic acid by the action of ribonuclease such as Dicer (WO 2005/089287), a double-stranded nucleic acid having no 3'-terminal or 5'-terminal overhang, or the like can also be used as the nucleic acid silencing the target gene.

When the double-stranded nucleic acid is siRNA, preferably, the antisense strand is an antisense strand in which a sequence of at least the 1st to 17th bases (nucleosides) counted from the 5' end toward the 3' end is a sequence of bases complementary to a sequence of 17 consecutive bases of the mRNA of the target gene. More preferably, the antisense strand is an antisense strand in which a sequence of the 1st to 19th bases counted from the 5' end toward the 3' end is a sequence of bases complementary to a sequence of 19 consecutive bases of the mRNA of the target gene, a sequence of the 1st to 21st bases counted from the 5' end toward the 3' end is a sequence of bases complementary to a sequence of 21 consecutive bases of the mRNA of the target gene, or a sequence of the 1st to 25th bases counted from the 5' end toward the 3' end is a sequence of bases complementary to a sequence of 25 consecutive bases of the mRNA of the target gene.

When the nucleic acid used in the present invention is siRNA, preferably 10 to 70%, more preferably 15 to 60%, further preferably 20 to 50%, of sugars in the nucleic acid is ribose substituted at position 2' with a modifying group. The ribose substituted at position 2' with a modifying group according to the present invention means that the hydroxy group at position 2' of the ribose is substituted with a modifying group. The resulting configuration may be the same as or different from that of the hydroxy group at position 2' of the ribose and is preferably the same as that of the hydroxy group at position 2' of the ribose. Examples of the modifying group in the ribose substituted at position 2' therewith include those listed in the definition of the modifying group in the 2'-modified nucleotide in the nucleotide modified at the sugar moiety, and a hydrogen atom. The modifying group is preferably 2'-cyano, 2'-halogen, 2'-O-cyano, 2'-alkyl, 2'-substituted alkyl, 2'-O-alkyl, 2'-O-substituted alkyl, 2'-O-alkenyl, 2'-O-substituted alkenyl, 2'-Se-alkyl, 2'-Se-substituted alkyl, or the like, more preferably 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O-[2-(methoxy)ethyl], 2'-O-(3-aminopropyl), 2'-O-[2-(N,N-dimethyl)aminooxy]ethyl, 2'-O-[3-(N,N-dimethylamino)propyl], 2'-O-{2-[2-(N,N-dimethylamino)ethoxy]ethyl}, 2'-O-[2-(methylamino)-2-oxoethyl], 2'-Se-methyl, a hydrogen atom, or the like, further preferably 2'-O-methyl, 2'-O-ethyl, 2'-fluoro, a hydrogen atom, or the like, most preferably 2'-O-methyl and 2'-fluoro.

The nucleic acid used in the present invention encompasses derivatives in which, for example, an oxygen atom contained in a phosphoric acid moiety, an ester moiety, or the like in the structure of the nucleic acid, or the like is substituted with a different atom such as a sulfur atom.

The hydroxy group at position 5' of a sugar attached to the 5' terminal base of the antisense strand or the sense strand may be modified with a phosphoric acid group or any of the aforementioned modifying groups, or with a group that is converted to a phosphoric acid group or any of the aforementioned modifying groups by an in vivo nucleolytic enzyme or the like.

The hydroxy group at position 3' of a sugar attached to the 3' terminal base of the antisense strand or the sense strand may be modified with a phosphoric acid group or any of the aforementioned modifying groups, or with a group that is converted to a phosphoric acid group or any of the aforementioned modifying groups by an in vivo nucleolytic enzyme or the like.

The single-stranded nucleic acid can be, for example, any nucleic acid consisting of a sequence complementary to a sequence consisting of 15 to 27 consecutive bases (nucleosides), preferably 15 to 25 consecutive bases, more preferably 15 to 23 consecutive bases, further preferably 15 to 21 consecutive bases, particularly preferably 15 to 19 consecutive bases, of the target gene, or any nucleic acid derived from the nucleic acid by the substitution, deletion or addition of 1 to 3 bases, preferably 1 or 2 bases, more preferably 1 base, and having silencing activity against the target protein. The single-stranded nucleic acid preferably consists of a sequence of 15 to 30 bases (nucleosides). More preferably, a single-stranded nucleic acid of 15 to 27 bases, further preferably 15 to 25 bases, particularly preferably 15 to 23 bases, is suitably used.

A linkage via a spacer sequence (spacer oligonucleotide) of the antisense strand and the sense strand constituting the double-stranded nucleic acid described above may be used as the single-stranded nucleic acid. The spacer oligonucleotide is preferably a single-stranded nucleic acid molecule of 6 to 12 bases. Its 5'-terminal sequence is preferably UU. Examples of the spacer oligonucleotide include a nucleic acid consisting of a sequence UUCAAGAGA. The order in which the antisense strand and the sense strand are linked via the spacer oligonucleotide can be any order in which either of the strands may be positioned on the 5' side. The single-stranded nucleic acid is preferably a single-stranded nucleic acid such as shRNA having a duplex formation moiety by, for example, a stem-loop structure. The single-stranded nucleic acid such as shRNA is usually 50 to 70 bases long.

A nucleic acid of 70 bases or smaller in length, preferably 50 bases or smaller in length, more preferably 30 bases or smaller in length, designed to form the single-stranded nucleic acid or the double-stranded nucleic acid by the action of ribonuclease or the like may be used.

The nucleic acid used in the present invention can be produced by use of a known RNA or DNA synthesis method and RNA or DNA modification method.

The composition of the present invention is a composition containing the compound of the present invention or a pharmaceutically acceptable salt thereof, and a nucleic acid, and may be a complex of, for example, the compound of the present invention or a pharmaceutically acceptable salt thereof, and a nucleic acid.

The composition of the present invention is a composition containing the compound of the present invention or a pharmaceutically acceptable salt thereof, a neutral lipid and/or a polymer, and a nucleic acid, and may be a complex of, for example, the compound of the present invention or a pharmaceutically acceptable salt thereof, a neutral lipid and/or a polymer, and a nucleic acid.

The composition of the present invention contains a lipid membrane, and the complex may be enclosed with the lipid membrane.

The lipid membrane may be a lipid monolayer (lipid monomolecular membrane) or a lipid bilayer (lipid bimolecular membrane). The compound of the present invention or a pharmaceutically acceptable salt thereof, and a neutral lipid and/or a polymer may be contained in the lipid membrane.

Also, a cationic lipid other than the cationic lipid corresponding to the compound of the present invention or a pharmaceutically acceptable salt thereof may be contained in the complex and/or the lipid membrane.

Hereinafter, the compound of the present invention or a pharmaceutically acceptable salt thereof is simply referred to as the "cationic lipid of the present invention" in some cases.

Other examples of the composition of the present invention also include a composition containing a complex of a cationic lipid other than the cationic lipid of the present invention and the nucleic acid, or a complex of a cationic lipid other than the cationic lipid of the present invention, a neutral lipid and/or a polymer and the nucleic acid, and a lipid membrane with which the complex is enclosed, wherein the cationic lipid of the present invention is contained in the lipid membrane, or the like. In this case as well, the lipid membrane may be a lipid monolayer (lipid monomolecular membrane) or a lipid bilayer (lipid bimolecular membrane). A cationic lipid other than the cationic lipid of the present invention, a neutral lipid and/or a polymer may be contained in the lipid membrane.

The composition of the present invention is preferably a composition containing a complex of the cationic lipid of the present invention and the nucleic acid, a composition containing a complex of the cationic lipid of the present invention and the nucleic acid, and a lipid membrane with which the complex is enclosed, wherein the cationic lipid of the present invention is contained in the lipid membrane, and a composition containing a complex of a cationic lipid other than the cationic lipid of the present invention and the nucleic acid, and a lipid membrane with which the complex is enclosed, wherein the cationic lipid of the present invention is contained in the lipid membrane, and more preferably a composition containing a complex of the cationic lipid of the present invention and the nucleic acid, and a lipid membrane with which the complex is enclosed, wherein the cationic lipid of the present invention is contained in the lipid membrane. In any of these compositions, a neutral lipid and/or a polymer may be contained in the lipid membrane. Also, a cationic lipid other than the cationic lipid of the present invention may be contained in the complex and/or the lipid membrane.

Examples of the form of the complex include a complex of the nucleic acid and a membrane (inverse micelle) consisting of a lipid monolayer (monomolecular layer), a complex of the nucleic acid and a liposome, and a complex of the nucleic acid and a micelle, or the like, and preferably include a complex of the nucleic acid and a membrane consisting of a lipid monolayer, and a complex of the nucleic acid and a liposome.

Examples of the composition containing the complex and a lipid membrane with which the complex is enclosed include a liposome containing the complex and a lipid bilayer with which the complex is enclosed, or the like.

One or more cationic lipids of the present invention may be used in the composition of the present invention, and also, one or more cationic lipids other than the cationic lipid of the present invention may be mixed in the composition of the present invention in addition to the cationic lipid of the present invention.

Examples of the cationic lipid other than the cationic lipid of the present invention include: N-[1-(2,3-dioleyloxy)propyl]-N,N,N-trimethylammonium chloride (DOTMA), N-(2,3-di-(9-(Z)-octadecenoyloxy))-prop-1-yl-N,N,N-trimethylammonium chloride (DOTAP), or the like, disclosed in Japanese Unexamined Patient Application Publication No. 61-161246 (U.S. Pat. No. 5,049,386); N-[1-(2,3-dioleyloxypropyl)]-N,N-dimethyl-N-hydroxyethyl ammonium bromide (DORIE), 2,3-dioleyloxy-N-[2-(sperminecarboxamide)ethyl]-N,N-dimethyl-1-propanaminium trifluoroacetic acid (DOSPA), or the like, disclosed WO 91/16024 and WO 97/019675; DLinDMA or the like, disclosed in WO 2005/121348; DLin-K-DMA disclosed in WO 2009/086558; and (3R,4R)-3,4-bis((Z)-hexadec-9-enyloxy)-1-methylpyrrolidine, N-methyl-N,N-bis(2-((Z)-octadec-6-enyloxy)ethyl) amine, or the like, disclosed in WO 2011/136368. Examples thereof preferably include cationic lipids having a tertiary amine site having two unsubstituted alkyl groups or a quaternary ammonium site having three unsubstituted alkyl groups, such as DOTMA, DOTAP, DORIE, DOSPA, 1,2-dilinoleyloxy-N,N-dimethylaminopropane (DLinDMA), and 2,2-dilinoleyl-4-dimethylaminomethyl-[1,3]-dioxolane (DLin-K-DMA), and more preferably include cationic lipids having the tertiary amine site. The unsubstituted alkyl groups in the tertiary amine site or the quaternary ammonium site are more preferably methyl groups.

The composition of the present invention can contain, in addition to the nucleic acid, a compound chemically analogous to the nucleic acid.

The composition of the present invention can be produced according to a production method known in the art or a method equivalent thereto and may be produced by any production method. For example, a liposome preparation method known in the art can be applied to the production of a composition containing a liposome, which is a composition. Examples of the liposome preparation method known in the art include a liposome preparation method of Bangham et al. [see "J. Mol. Biol.", 1965, Vol. 13, p. 238-252], an ethanol injection method [see "J. Cell Biol.", 1975, Vol. 66, p. 621-634], a French press method [see "FEBS Lett.", 1979, Vol. 99, p. 210-214], a freezing-thawing method [see "Arch. Biochem. Biophys.", 1981, Vol. 212, p. 186-194], a reverse-phase evaporation method [see "Proc. Natl. Acad. Sci. USA", 1978, Vol. 75, p. 4194-4198], a pH gradient method (see e.g., Japanese Patent Nos. 2572554 and 2659136 or the like), or the like. For example, water, an acid, an alkali, various buffer solutions, physiological saline, an amino acid transfusion of the like can be used as a solution for dispersing the liposome in the production of the liposome. In the production of the liposome, for example, an antioxidant such as citric acid, ascorbic acid, cysteine, or ethylenediaminetetraacetic acid (EDTA); or a tonicity agent such as glycerin, glucose, or sodium chloride, or the like may also be added. Alternatively, the liposome can also be produced, for example, by dissolving the cationic lipid of the present invention, a mixture of the cationic lipid of the present invention and a cationic lipid other than the cationic lipid of the present invention, or the like, for example, in an organic solvent such as ethanol, distilling off the solvent, then adding physiological saline or the like to the residue, and shaking and stirring the mixture to form the liposome.

Also, the composition of the present invention can be produced by, for example, a production method which involves dissolving the cationic lipid of the present invention, or a mixture of the cationic lipid of the present invention and a cationic lipid other than the cationic lipid of the present invention in chloroform in advance, subsequently adding an aqueous solution of the nucleic acid and methanol to the solution, mixing the mixture to form a cationic lipid/nucleic acid complex, further isolating the chloroform layer, and adding thereto polyethylene glycolated phospholipid, a neutral lipid and water to form a water-in-oil (W/O) emulsion, which is then treated by the reverse-phase evaporation method (see Japanese Unexamined Paten Application Publication Translation of PCT Application) No. 2002-508765), or a production method which involves dissolving the nucleic acid in an aqueous solution of an acidic electrolyte, adding, for example, a mixture of the cationic lipid of the present invention, or a mixture of the cationic lipid of the present invention and a cationic lipid other than the cationic lipid of the present invention (in ethanol) to the solution, decreasing the ethanol concentration to 20 v/v % to prepare a liposome containing the nucleic acid, removing excessive ethanol by dialysis after sizing and filtration, and then dialyzing the sample by further elevating pH to remove the nucleic acid attached to the surface of the composition (see Japanese Unexamined Patent Application Publication (Translation of PCT Application) No. 2002-501511 and Biochimica et Biophysica Acta, 2001, Vol. 1510, p. 152-166), or the like.

Among the compositions of the present invention, a composition containing a liposome containing a complex of the cationic lipid of the present invention and the nucleic acid, or a complex of the cationic lipid of the present invention, a neutral lipid and/or a polymer and the nucleic acid, and a lipid bilayer with which the complex is enclosed can be produced according to production methods described in, for example, WO 02/28367 and WO 2006/080118 or the like.

When the composition of the present invention is produced according to a production method described in WO02/28367, WO2006/080118 or the like, the composition of the present invention can be obtained by producing a complex by using components appropriately selected from the cationic lipid of the present invention, a nucleic acid, a neutral lipid and/or a polymer, and a cationic lipid other than the cationic lipid of the present invention, dispersing the resultant complex, without dissolution, in water or a 0 to 40% aqueous ethanol solution (liquid A), and aside from this, dissolving a lipid membrane component for enclosing the complex, for example, in an aqueous ethanol solution (liquid B), mixing the liquid A and the liquid B in equal amounts or at a volume ratio of 1:1 to 7:3, and further appropriately adding water thereto. One or more cationic lipids of the present invention or cationic lipids other than the cationic lipid of the present invention can be used as cationic lipids in the liquids A and B. Alternatively, the cationic lipid of the present invention and the cationic lipid other than the cationic lipid of the present invention may be combined and used as a mixture.

In the present invention, during and after production of, for example, the composition containing a complex of the cationic lipid of the present invention and the nucleic acid, or a complex of the cationic lipid of the present invention, a neutral lipid and/or a polymer and the nucleic acid, and a lipid membrane with which the complex is enclosed, the composition containing a complex of a cationic lipid other than the cationic lipid of the present invention and the nucleic acid, or a complex of a cationic lipid other than the cationic lipid of the present invention, a neutral lipid and/or a polymer and the nucleic acid, and a lipid membrane with which the complex is enclosed, wherein the cationic lipid of the present invention is contained in the lipid membrane, or the like, the structures of the complex and the membrane may be varied due to the electrostatic interaction between the nucleic acid in the complex and the cationic lipid in the lipid membrane, or the fusion of the cationic lipid in the complex with the cationic lipid in the lipid membrane, and such a composition is also included in the composition of the present invention.

The composition containing the cationic lipid of the present invention and the nucleic acid can also be obtained according to production methods described in, for example, WO 02/28367 and WO 2006/080118, or the like, by producing a complex of the nucleic acid, preferably the double-stranded nucleic acid, and a liposome containing the cationic lipid of the present invention and/or a cationic lipid other than the cationic lipid of the present invention, dispersing the complex in water or a 0 to 40% aqueous ethanol solution without dissolution (liquid A), aside from this, dissolving the cationic lipid of the present invention and/or a cationic lipid other than the cationic lipid of the present invention in an aqueous ethanol solution (liquid B), mixing the liquid A and the liquid B in equal amounts or at a volume ratio of 1:1 to 7:3, and further appropriately adding water thereto. The composition obtained by this production method is preferably a composition containing a complex of the cationic lipid and the nucleic acid, and a lipid membrane with which the complex is enclosed, or a composition containing a complex of the cationic lipid and a membrane (inverse micelle) consisting of a lipid monolayer containing the nucleic acid, and a lipid membrane with which the complex is enclosed. In these cases, the lipid membrane may be a lipid monolayer (lipid monomolecular membrane) or a lipid bilayer (lipid bimolecular membrane).

The liposome in the complex of the nucleic acid and the liposome as disclosed herein is preferably a liposome size-adjusted in advance to an average particle size of 10 nm to 400 nm, more preferably 20 nm to 110 nm, further preferably 30 nm to 80 nm. A neutral lipid and/or a polymer may be contained in the complex and/or the lipid membrane. The liquid A may have an ethanol concentration of 20 to 70% as long as the complex of the liposome and the nucleic acid can be formed.

Instead of mixing the liquid A and the liquid B in equal amounts, the liquid A and the liquid B may be mixed at a ratio that does not dissolve the complex after the mixing and adjusts an ethanol concentration so as not to dissolve the cationic lipid in the liquid B. Preferably, the liquid A and the liquid B may instead be mixed at a ratio that neither dissolves the complex nor the cationic lipid in the liquid B and creates an aqueous ethanol solution having an ethanol concentration of 30 to 60%. Alternatively, the liquid A and the liquid B may be mixed at a ratio that adjusts an ethanol concentration so as not to dissolve the complex after the mixing of the liquid A and the liquid B, and the ethanol concentration is further adjusted by the addition of water so as not to dissolve the cationic lipid in the liquid B.

The complex of the nucleic acid and the liposome in the liquid A as disclosed herein is morphologically converted to a complex of a membrane (inverse micelle) consisting of a lipid monolayer containing the cationic lipid and the nucleic acid after the mixing of the liquid A and the liquid B and the further appropriate addition of water. The composition containing the nucleic acid and the cationic lipid obtained by the production method as disclosed herein is preferably a composition containing a complex of the cationic lipid and the nucleic acid, and a lipid membrane with which the complex is enclosed, or a composition containing a complex of a membrane (inverse micelle) consisting of a lipid monolayer containing the cationic lipid and the nucleic acid, and a lipid membrane with which the complex is enclosed, wherein the cationic lipid is contained in the lipid membrane. Such a composition is excellent in productivity (yield and/or homogeneity).

In the composition of the present invention, the total number of molecules of the cationic lipid of the present invention in the complex is preferably 0.5 to 4 times, more preferably 1.5 to 3.5 times, further preferably 2 to 3 times the number of phosphorus atoms of the nucleic acid. The total number of molecules of the cationic lipid of the present invention and the cationic lipid other than the cationic lipid of the present invention in the complex is preferably 0.5 to 4 times, more preferably 1.5 to 3.5 times, further preferably 2 to 3 times the number of phosphorus atoms of the nucleic acid.

In the composition of the present invention, the total number of molecules of the cationic lipid of the present invention in the composition containing the complex and a lipid membrane with which the complex is enclosed is preferably 1 to 10 times, more preferably 2.5 to 9 times, further preferably 3.5 to 8 times the number of phosphorus atoms of the nucleic acid. The total number of molecules of the cationic lipid of the present invention and the cationic lipid other than the cationic lipid of the present invention in this composition is preferably 1 to 10 times, more preferably 2.5 to 9 times, further preferably 3.5 to 8 times the number of phosphorus atoms of the nucleic acid.

The neutral lipid can be any of simple lipids, complex lipids, and derived lipids. Examples thereof include, but are not limited to phospholipids, glyceroglycolipids, sphingoglycolipids, sphingoid, sterol, or the like.

When the composition of the present invention contains a neutral lipid, the total number of molecules of the neutral lipid is preferably 0.1 to 2 times, more preferably 0.2 to 1.5 times, further preferably 0.3 to 1.2 times the total number of molecules of the cationic lipid of the present invention and the cationic lipid other than the cationic lipid of the present invention. In any composition of the present invention, the neutral lipid may be contained in the complex or may be contained in the lipid membrane with which the complex is enclosed. More preferably, the neutral lipid is contained at least in the lipid membrane with which the complex is enclosed. Further preferably, the neutral lipid is contained in both of the complex and the lipid membrane with which the complex is enclosed.

Examples of the phospholipid as the neutral lipid include natural or synthetic phospholipids such as phosphatidylcholines (specifically, soybean phosphatidylcholine, egg phosphatidylcholine (EPC), distearoyl phosphatidylcholine (DSPC), dipalmitoyl phosphatidylcholine (DPPC), palmitoyl oleoyl phosphatidylcholine (POPC), dimyristoyl phosphatidylcholine (DMPC), dioleoyl phosphatidylcholine (DOPC), etc.), phosphatidylethanolamines (specifically distearoyl phosphatidylethanolamine (DSPE), dipalmitoyl phosphatidylethanolamine (DPPE), dioleoyl phosphatidylethanolamine (DOPE), dimyristoyl phosphatidylethanolamine (DMPE), 16-0-monomethyl PE, 16-0-dimethyl PE, 18-1-trans PE, palmitoyl oleoyl-phosphatidylethanolamine (POPE), 1-stearoyl-2-oleoyl-phosphatidylethanolamine (SOPE), etc.), glycerophospholipids (specifically, phosphatidylserine, phosphatidic acid, phosphatidylglycerol, phosphatidylinositol, palmitoyl oleoyl phosphatidylglycerol (POPG), lysophosphatidylcholine, etc.), sphingophospholipids (specifically, sphingomyelin, ceramide phosphoethanolamine, ceramide phosphoglycerol, ceramide phosphoglycerophosphoric acid, etc.), glycerophosphonolipids, sphingophosphonolipids, natural lecithins (specifically, egg lecithin, soybean lecithin, etc.), hydrogenated phospholipids (specifically, hydrogenated soybean phosphatidylcholine, etc.), or the like.

Examples of the glyceroglycolipid as the neutral lipid include sulfoxyribosyl glyceride, diglycosyl diglyceride, digalactosyl diglyceride, galactosyl diglyceride, glycosyl diglyceride, or the like.

Examples of the sphingoglycolipid as the neutral lipid include galactosyl cerebroside, lactosyl cerebroside, ganglioside, or the like.

Examples of the sphingoid as the neutral lipid include sphingan, icosasphingan, sphingosine, and derivatives of the foregoing, or the like. Examples of the derivatives include substances derived from sphingan, icosasphingan, sphingosine, or the like by the conversion of —$NH_2$ to —$NHCO(CH_2)_xCH_3$ wherein x is an integer from 0 to 18 and is particularly preferably 6, 12, or 18).

Examples of the sterol as the neutral lipid include cholesterol, dihydrocholesterol, lanosterol, β-sitosterol, campesterol, stigmasterol, brassicasterol, erugosterol, fucosterol, 3β-[N—(N',N'-dimethylaminoethyl)carbamoyl]cholesterol (DC-Chol), or the like.

Examples of the polymer include polymers such as proteins, albumin, dextran, Polyfect, chitosan, dextran sulfate, poly-L-lysine, polyethylenimine, polyaspartic acid, styrene-maleic acid copolymers, isopropylacrylamide-acrylpyrrolidone copolymers, polyethylene glycol-modified dendrimers, polylactic acid, polylactic acid-polyglycolic acid, and polyethylene glycolated polylactic acid, micelles consisting of one or more of salts of the foregoing, or the like.

In this context, the salt of the polymer encompasses metal salts, ammonium salts, acid-addition salts, organic amine-addition salts, amino acid-addition salts, or the like. Examples of the metal salts include: alkali metal salts such as lithium salt, sodium salt, and potassium salt; alkaline earth metal salts such as magnesium salt and calcium salt; aluminum salts; and zinc salts, or the like. Examples of the ammonium salts include salts of ammonium, tetramethylammonium, or the like. Examples of the acid-addition salts include: inorganic acid salts such as hydrochloride, sulfate, nitrate, and phosphate; and organic acid salts such as acetate, maleate, fumarate, and citrate. Examples of the organic amine-addition salts include addition salts of morpholine, piperidine, or the like. Examples of the amino acid-addition salts include addition salts of glycine, phenylalanine, aspartic acid, glutamic acid, lysine, or the like.

Also, any composition of the present invention preferably contains a lipid derivative or a fatty acid derivative of one or more substances selected from, for example, sugars, peptides, nucleic acids and water-soluble polymers, a surfactant, or the like. The derivative, the surfactant or the like may be contained in the complex or may be contained in the lipid membrane with which the complex is enclosed, and is more preferably contained in both of the complex and the lipid membrane with which the complex is enclosed.

When the composition of the present invention contains a lipid derivative or a fatty acid derivative of one or more substances selected from sugars, peptides, nucleic acids, and water-soluble polymers, the total number of molecules of the lipid derivative or the fatty acid derivative of one or more substances selected from sugars, peptides, nucleic acids, and water-soluble polymers is preferably 0.01 to 0.3 times, more preferably 0.02 to 0.25 times, further preferably 0.03 to 0.15 times the total number of molecules of the cationic lipid of the present invention and the cationic lipid other than the cationic lipid of the present invention.

Examples of the lipid derivative or the fatty acid derivative of one or more substances selected from sugars, peptides, nucleic acids, and water-soluble polymers, or the surfactant preferably include glycolipids, and lipid derivatives or fatty acid derivatives of water-soluble polymers and more preferably include lipid derivatives or fatty acid derivatives of water-soluble polymers. The lipid derivative or the fatty acid derivative of one or more substances selected from sugars, peptides, nucleic acids, and water-soluble polymers, or the surfactant is preferably a two-faced substance in which a part of the molecule has the properties of binding to other constituents of the composition via, for example, hydrophobic affinity, electrostatic interaction, or the like and the other moiety has the properties of binding to a solvent for use in the production of the composition via, for example, hydrophilic affinity, electrostatic interaction, or the like.

Examples of the lipid derivatives or the fatty acid derivatives of sugars, peptides or nucleic acids include substances obtained by the binding of sugars such as sucrose, sorbitol, and lactose, peptides such as casein-derived peptides, ovalbumin-derived peptides, soybean-derived peptides, and glutathione, or nucleic acids such as DNA, RNA, plasmids, siRNA, and ODN to the neutral lipids or the cationic lipids of the present invention listed in the definition of the composition or to fatty acids such as stearic acid, palmitic acid, myristic acid, and lauric acid, or the like.

Examples of the lipid derivatives or the fatty acid derivatives of sugars also include the glyceroglycolipids or the sphingoglycolipids listed in the definition of the composition, or the like.

Examples of the lipid derivatives or the fatty acid derivatives of water-soluble polymers include substances obtained by the binding of polyethylene glycol, polyglycerin, polyethylenimine, polyvinyl alcohol, polyacrylic acid, polyacrylamide, oligosaccharide, dextrin, water-soluble cellulose, dextran, chondroitin sulfate, polyglycerin, chitosan, polyvinylpyrrolidone, polyaspartic acid amide, poly-L-lysine, mannan, pullulan, oligoglycerol, or the like or derivatives of the foregoing to the neutral lipids or the cationic lipids of the present invention listed in the definition of the composition or to fatty acids such as stearic acid, palmitic acid, myristic acid, and lauric acid, salts of the foregoing. Examples thereof more preferably include lipid derivatives or fatty acid derivatives of polyethylene glycol or polyglycerin, and salts of the foregoing and further preferably include lipid derivatives or fatty acid derivatives of polyethylene glycol and salts of the foregoing.

Examples of the lipid derivatives or the fatty acid derivatives of polyethylene glycol include polyethylene glycolated lipids [specifically, polyethylene glycol-phosphatidylethanolamine (more specifically, 1,2-distearoyl-sn-glycero-3-phosphoethanolamine-N-[methoxy(polyethylene glycol)-2000] (PEG-DSPE), 1,2-dimyristoyl-sn-glycero-3-phosphoethanolamine-N-[methoxy(polyethylene glycol)-2000] (PEG-DMPE), etc.), polyoxyethylene hydrogenated castor oil 60, CREMOPHOR EL, etc.], polyethylene glycol sorbitan fatty acid esters (specifically, polyoxyethylene sorbitan monooleate, etc.), or the like, and polyethylene glycol fatty acid esters and more preferably include polyethylene glycolated lipids.

Examples of the lipid derivatives or the fatty acid derivatives of polyglycerin include polyglycerinated lipids (specifically, polyglycerin-phosphatidylethanolamine, etc.), polyglycerin fatty acid esters, or the like and more preferably include polyglycerinated lipids.

Examples of the surfactant include polyoxyethylene sorbitan monooleate (specifically, polysorbate 80, etc.), polyoxyethylene polyoxypropylene glycol (specifically, Pluronic F68, etc.), sorbitan fatty acid esters (specifically, sorbitan monolaurate, sorbitan monooleate, etc.), polyoxyethylene derivatives (specifically, polyoxyethylene hydrogenated castor oil 60, polyoxyethylene lauryl alcohol, etc.), glycerin fatty acid esters, polyethylene glycol alkyl ethers, or the like and preferably include polyoxyethylene polyoxypropylene glycol, glycerin fatty acid esters and polyethylene glycol alkyl ethers.

The complex and the lipid membrane in the composition of the present invention can each be arbitrarily surface-modified with, for example, a water-soluble polymer or the like [see D. D. Lasic and F. Martin ed., "Stealth Liposomes" (USA), CRC Press Inc., 1995, p. 93-102]. Examples of the water-soluble polymer that may be used in the surface modification include polyethylene glycol, polyglycerin, polyethylenimine, polyvinyl alcohol, polyacrylic acid, polyacrylamide, oligosaccharides, dextrin, water-soluble cellulose, dextran, chondroitin sulfate, polyglycerin, chitosan, polyvinylpyrrolidone, polyaspartic acid amide, poly-L-lysine, mannan, pullulan, oligoglycerol, or the like and preferably include dextran, pullulan, mannan, amylopectin, hydroxyethyl starch, or the like. The lipid derivative, the fatty acid derivative of one or more substances selected from sugars, peptides, nucleic acids, and water-soluble polymers (as defined above), or the like can also be used in the surface modification. The surface modification is a method for allowing the complex and the lipid membrane in the composition of the present invention to contain the lipid derivative or the fatty acid derivative of one or more substances selected from sugars, peptides, nucleic acids, and water-soluble polymers, or the surfactant.

A targeting ligand can be arbitrarily bonded directly to the surface of the composition of the present invention through a covalent bond to a polar head residue of a lipid component in the composition of the present invention (see WO 2006/116107).

The average particle size of the complex or the lipid membrane with which the complex is enclosed in the composition of the present invention can be arbitrarily selected, if desired, and is preferably set to an average particle size described below. Examples of a method for adjusting the average particle size include an extrusion method and a method of mechanically pulverizing a large multilamellar vesicle (MLV) or the like (specifically, using Manton Gaulin, Microfluidizer, etc.) [see R. H. Muller, S. Benita and B. Bohm ed., "Emulsion and Nanosuspensions for the Formulation of Poorly Soluble Drugs", Germany, Scientific Publishers Stuttgart, 1998, p. 267-294], or the like.

The size of the complex in the composition of the present invention is preferably approximately 5 nm to 200 nm, more preferably approximately 20 nm to 150 nm, further preferably approximately 30 nm to 100 nm, in terms of an average particle size.

The size of the composition of the present invention (the lipid membrane with which the complex is enclosed) is preferably approximately 10 nm to 300 nm, more preferably approximately 30 nm to 200 nm, further preferably approximately 50 nm to 150 nm, in terms of an average particle size.

The average particle size of the complex or the lipid membrane with which the complex is enclosed in the composition of the present invention can be measured by, for example, a dynamic light scattering method.

The nucleic acid in the composition of the present invention can be introduced into a cell by introducing the composition of the present invention into a mammalian cell.

The introduction of the composition of the present invention into a mammalian cell can be performed according to procedures of transfection known in the art that can be performed in vivo. For example, the composition of the present invention can be intravenously administered to a mammal including a human and thereby delivered to, for example, an organ or a site having tumor or inflammation so that the nucleic acid in the composition of the present invention is introduced into a cell of the organ or the site that has received the composition. Examples of the organ or the site having tumor or inflammation include, but are not particularly limited to, the stomach, the large intestine, the liver, the lung, the spleen, the pancreas, the kidney, the bladder, the skin, vascular vessels, eye balls, or the like. Also, the composition of the present invention can be intravenously administered to a mammal including a human and thereby delivered to, for example, the liver, the lung, the spleen, and/or the kidney so that the nucleic acid in the composition of the present invention is introduced into a cell of the organ or the site that has received the composition. The cell of the liver, the lung, the spleen, and/or the kidney can be any of normal cells, cells related to tumor or inflammation, and cells related to the other diseases.

Provided that the nucleic acid in the composition of the present invention is a nucleic acid having a silencing effect on a target gene through the use of RNA interference (RNAi), for example, the nucleic acid silencing a target gene or the like can be introduced into a mammalian cell in vivo. As a result, the expression of the target gene can be suppressed. The recipient is preferably a human.

Provided that the target gene in the present invention is, for example, a gene expressed in the liver, the lung, the kidney, or the spleen, the composition of the present invention can be used as a therapeutic agent or a prophylactic agent for a disease related to the liver, the lung, the kidney, or the spleen. Specifically, the present invention also provides a method for treating a disease related to the liver, the lung, the kidney, or the spleen, comprising administering the composition of the present invention described above to a mammal. The recipient is preferably a human, more preferably a human having the disease related to the liver, the lung, the kidney, or the spleen.

The composition of the present invention can also be used as a tool for verifying the effectiveness of suppression of a target gene in an in vivo drug efficacy evaluation model as to a therapeutic agent or a prophylactic agent for a disease related to the liver, the lung, the kidney, or the spleen.

The composition of the present invention can also be used as a preparation aimed at, for example, stabilizing the nucleic acid in a biogenic substance such as a blood component (e.g., in blood, the digestive tract, of the like), reducing adverse reactions, enhancing drug accumulation to a tissue or an organ containing an expression site of the target gene, or the like.

When the composition of the present invention is pharmaceutically used as a therapeutic agent or a prophylactic agent for, for example, a disease related to the liver, the lung, the kidney, or the spleen, or the like, an administration route most effective for treatment is desirably used. Examples of such an administration route can include parenteral or oral administration such as administration into the oral cavity, intratracheal administration, intrarectal administration, subcutaneous administration, intramuscular administration, intravenous administration, or the like. Examples thereof can preferably include intravenous administration and intramuscular administration and more preferably include intravenous administration.

The dose differs depending on the pathological condition or age of the recipient, the administration route, or the like. For example, the composition of the present invention can be administered, for example, at a daily dose of approximately 0.1 µg to 1000 mg in terms of the amount of the nucleic acid.

Examples of the preparation suitable for intravenous administration or intramuscular administration include injections. A dispersion of the composition prepared by the aforementioned method may be used directly in the form of, for example, an injection or the like. Alternatively, the dispersion may be used after removal of the solvent by, for example, filtration, centrifugation, or the like, or the dispersion may be used after being freeze-dried and/or may be used after being supplemented with, for example, an excipient such as mannitol, lactose, trehalose, maltose, glycine, or the like and then freeze-dried.

In the case of an injection, the dispersion of the composition or the solvent-free or freeze-dried composition described above is preferably mixed with, for example, water, an acid, an alkali, various buffer solutions, physiological saline, an amino acid transfusion, or the like to prepare the injection. Alternatively, the injection may be prepared by the addition of, for example, an antioxidant such as citric acid, ascorbic acid, cysteine, or EDTA or a tonicity agent such as glycerin, glucose or sodium chloride. Also, the injection can also be cryopreserved by the addition of a cryopreserving agent such as glycerin.

Next, the present invention will be specifically described with reference to Examples and Test Examples. However, the present invention is not intended to be limited by these Examples and Test Examples.

Proton nuclear magnetic resonance spectra ($^1$H NMR) shown in Examples were measured at 400 MHz, and no exchangeable proton may be clearly observed depending on compounds and measurement conditions. The multiplicity of signals is indicated as usually used.

Example 1

2-Methyl-1,3-bis((9Z,12Z)-octadeca-9,12,-dien-1-yloxy)propan-2-amine (Compound 1)

2-Amino-2-methylpropane-1,3-diol (manufactured by Tokyo Chemical Industry Co., Ltd., 0.300 g, 4.76 mmol) was dissolved in tetrahydrofuran (3 mL), and sodium hydride (60% oil, 0.171 g, 7.13 mmol) was added thereto at room temperature. After foaming was completed, (9Z,12Z)-octadeca-9,12-dienyl methanesulfonate (manufactured by Nu-Chek Pre, Inc., 2.458 g, 7.13 mmol) was added thereto, followed by stirring under heating to reflux for 2 hours. A saturated ammonium chloride aqueous solution was added to the resultant reaction mixture, followed by extraction with ethyl acetate. The organic layer was washed with saturated saline, dried over anhydrous magnesium sulfate, and filtered. The resultant filtrate was concentrated under reduced pressure, and the obtained residue was purified by silica gel column chromatography (chloroform/methanol=100/0 to 90/10) to obtain compound 1 (0.280 g, yield: 16%).

ESI-MS m/z: 602 (M+H)$^+$; $^1$H-NMR (CDCl$_3$) δ: 0.89 (t, J=7.0 Hz, 6H), 1.03 (s, 3H), 1.24-1.38 (m, 32H), 1.49-1.58 (m, 4H), 2.05 (q, J=6.8 Hz, 8H), 2.77 (t, J=6.7 Hz, 4H), 3.20 (d, J=8.6 Hz, 2H), 3.24 (d, J=8.6 Hz, 2H), 3.41 (t, J=6.6 Hz, 4H), 5.29-5.44 (m, 8H).

Example 2

N,N,2-Trimethyl-1,3-bis((9Z,12Z)-octadeca-9,12-dien-1-yloxy)propan-2-amine (Compound 2)

Compound 1 (0.240 g, 0.399 mmol) was dissolved in a mixed solvent of 1,2-dichloroethane (1 mL) and methanol (1 mL), formaldehyde (manufactured by Wako Pure Chemical Industries Ltd., 37% aqueous solution, 0.144 mL, 1.99 mmol) and sodium triacetoxyborohydride (manufactured by Tokyo Chemical Industry Co., Ltd., 0.211 g, 0.997 mmol) were added thereto, followed by stirring overnight at room temperature. Water was added to the resultant reaction mixture, and the aqueous layer was extracted with ethyl acetate. The organic layer was washed with saturated sodium bicarbonate, dried over anhydrous magnesium sulfate, and then filtered. The resultant filtrate was concentrated under reduced pressure, and the obtained residue was purified by NH silica gel column chromatography (hexane/ethyl acetate=99/1 to 80/20) to obtain compound 2 (0.191 g, yield: 76%).

ESI-MS m/z: 630 (M+H)$^+$; $^1$H-NMR (CDCl$_3$) δ: 0.89 (t, J=7.0 Hz, 6H), 0.95 (s, 3H), 1.26-1.39 (m, 32H), 1.53-1.58 (m, 4H), 2.05 (q, J=6.9 Hz, 8H), 2.31 (s, 6H), 2.77 (t, J=6.3 Hz, 4H), 3.33-3.42 (m, 8H), 5.27-5.43 (m, 8H).

Reference Example 1

N-Methyl-N-(2-methyl-1,3-bis((9Z,12Z)-octadeca-9,12-dien-1-yloxy)propan-2-yl)-2-nitrobenzenesulfonamide (Compound IIc-1)

Step 1

Compound 1 (0.500 g, 0.831 mmol) obtained in Example 1 was dissolved in dichloromethane (3 mL), triethylamine (manufactured by Wako Pure Chemical Industries Ltd., 2.55 mL, 18.3 mmol) and 2-nitrobenzene-1-sulfonyl chloride (manufactured by Sigma-Aldrich Corp., 0.368 g, 1.66 mmol) were added thereto under ice cooling, and the resultant was returned to room temperature, followed by stirring for 1 hour. Water was added to the resultant reaction mixture, followed by extraction with hexane. The organic layer was washed with saturated saline, dried over anhydrous magnesium sulfate, and filtered. The resultant filtrate was concentrated under reduced pressure, and the obtained residue was purified by the silica gel column chromatography (hexane/ethyl acetate=99/1 to 85/15) to obtain N-(2-methyl-1,3-bis((9Z,12Z)-octadeca-9,12-dien-1-yloxy)propan-2-yl)-2-nitrobenzenesulfonamide (0.400 g, yield: 61%).

ESI-MS m/z: 787 (M+H)$^+$

Step 2

N-(2-Methyl-1,3-bis((9Z,12Z)-octadeca-9,12-dien-1-yloxy)propan-2-yl)-2-nitrobenzenesulfonamide (0.200 g, 0.274 mmol) obtained in step 1 was dissolved in tetrahydrofuran (3 mL), cesium carbonate (manufactured by Wako Pure Chemical Industries Ltd., 0.248 g, 0.726 mmol) and methyl iodide (manufactured by Tokyo Chemical Industry Co., Ltd., 0.048 mL, 0.762 mmol) were added thereto, followed by stirring at 70° C. for 1 hour using a microwave reaction apparatus. Water was added to the resultant reaction mixture, followed by extraction with hexane. The organic layer was washed with saturated saline, dried over anhydrous magnesium sulfate, and filtered. The resultant filtrate was concentrated under reduced pressure to obtain a crude product of compound IIc-1 (0.200 g, yield: 91%).

ESI-MS m/z: 801 (M+H)$^+$

Example 3

N,2-Dimethyl-1,3-bis((9Z,12Z)-octadeca-9,12-dien-1-yloxy)propan-2-amine (Compound 3)

N-Methyl-N-(2-methyl-1,3-bis((9Z,12Z)-octadeca-9,12-dien-1-yloxy)propan-2-yl)-2-nitrobenzenesulfonamide (0.200 g, 0.250 mmol) obtained in Reference Example 1 was dissolved in acetonitrile (2 mL), 1-dodecanethiol (manufactured by Tokyo Chemical Industry Co., Ltd., 0.149 mL, 0.624 mmol) and 1,8-diazabicyclo[5.4.0]-7-undecene (manufactured by Nacalai Tesque, Inc., 0.0940 mL, 0.624 mmol) were added thereto, followed by stirring at 80° C. for 1 hour. Water was added to the resultant reaction mixture, and the aqueous layer was extracted with hexane. The organic layer was washed with saturated saline, dried over anhydrous magnesium sulfate, and then filtered and concentrated under reduced pressure. The obtained residue was purified by the NH silica gel column chromatography (hexane/ethyl acetate=90/10 to 75/25) to obtain compound 3 (0.070 g, yield: 46%).

ESI-MS m/z: 616 (M+H)$^+$; $^1$H-NMR (CDCl$_3$) δ: 0.89 (t, J=6.8 Hz, 6H), 1.02 (s, 3H), 1.25-1.40 (m, 32H), 1.50-1.59

(m, 4H), 2.05 (q, J=6.8 Hz, 8H), 2.32 (s, 3H), 2.77 (t, J=6.3 Hz, 4H), 3.26 (s, 4H), 3.40 (t, J=6.6 Hz, 4H), 5.28-5.43 (m, 8H).

Reference Example 2

N-Ethyl-2-methyl-1,3-bis((9Z,12Z)-octadeca-9,12-dien-1-yloxy)propan-2-amine (Compound IIc-2)

Compound IIc-2 (0.100 g, overall yield: 32%) was obtained in the same way as in Reference Example 1 by using ethyl iodide (manufactured by Nacalai Tesque, Inc.) instead of methyl iodide used in step 2.
ESI-MS m/z: 815 (M+H)$^+$ Example 4

N-Ethyl-2-methyl-1,3-bis((9Z,12Z)-octadeca-9,12-dien-1-yloxy)propan-2-amine (Compound 4)

Compound 4 (0.045 g, yield: 58%) was obtained in the same way as in Example 3 by using compound IIc-2 of Reference Example 2 instead of compound IIc-1 of Reference Example 1.
ESI-MS m/z: 630 (M+H)$^+$; $^1$H-NMR (CDCl$_3$) δ: 0.89 (t, J=7.0 Hz, 6H), 1.04 (s, 3H), 1.08 (t, J=6.8 Hz, 3H), 1.24-1.40 (i, 32H), 1.48-1.57 (i, 4H), 2.05 (q, J=6.8 Hz, 8H), 2.59 (q, J=6.8 Hz, 2H), 2.77 (t, J=6.3 Hz, 4H), 3.26 (d, J=8.9 Hz, 2H), 3.29 (d, J=8.9 Hz, 2H), 3.40 (t, J=6.6 Hz, 4H), 5.28-5.44 (m, 8H).

Reference Example 3

11,11'-((2-Methyl-2-((N-methyl-2-nitrophenyl)sulfonamide)propane-1,3-diyl)bis(oxy))diundecanoic Acid (Compound IIe-1)

Step 1

Compound IIc-1 (1.80 g, 2.09 mmol) obtained in Reference Example 1 was dissolved in tetrahydrofuran (8 mL), osmium tetroxide (manufactured by Wako Pure Chemical Industries Ltd., 10 wt % microencapsulation reagent, 0.106 g, 0.0420 mmol), N-methylmorpholine-N-oxide (manufactured by Nacalai Tesque, Inc., 1.10 g, 9.40 mmol) and water (2 mL) were added thereto, followed by stirring at room temperature all night. After assuring progression of the reaction to tetraol, an aqueous solution (2 mL) of sodium periodate (manufactured by Nacalai Tesque, Inc., 2.24 g, 10.5 mmol) was added thereto, followed by stirring at room temperature for 3 hours. Water was added to the resultant reaction mixture, and the aqueous layer was extracted with chloroform. The organic layer was washed with saturated saline, dried over anhydrous magnesium sulfate, and then filtered and concentrated under reduced pressure. The obtained residue was purified by the silica gel column chromatography (hexane/ethyl acetate=80/20 to 50/50) to obtain N-methyl-N-(2-methyl-1,3-bis((11-oxoundecyl)oxy)propan-2-yl)-2-nitrobenzenesulfonamide (1.00 g, yield: 75%).
ESI-MS m/z: 640 (M+H)$^+$ Step 2

N-Methyl-N-(2-methyl-1,3-bis((11-oxoundecyl)oxy)propan-2-yl)-2-nitrobenzenesulfonamide (1.30 g, 2.03 mmol) obtained in step 1 was dissolved in acetone (15 mL), and Jones reagent (manufactured by Sigma-Aldrich Corp., 2 mol/L chromium trioxide, 2.03 mL, 4.06 mmol) was added thereto under ice cooling, followed by stirring at room temperature for 5 minutes. Excessive Jones reagent was quenched with 2-propanol, and then a solid resulting from the reaction was removed by filtration. A 10% aqueous citric acid solution was added to the resultant filtrate, followed by extraction with ethyl acetate. The organic layer was washed with saturated saline, dried over anhydrous magnesium sulfate and then filtered. The obtained residue was concentrated under reduced pressure to obtain a crude product of compound IIe-1 (1.30 g, yield: 95%).
ESI-MS m/z: 671 (M–H)$^-$ Reference Example 4

Di((Z)-non-2-en-1-yl)11,11'-((2-methyl-2-((N-methyl-2-nitrophenyl)sulfonamide)propane-1,3-diyl)bis(oxy))diundecanoate (Compound IIc''-1)

11,11'-((2-Methyl-2-((N-methyl-2-nitrophenyl)sulfonamide)propane-1,3-diyl)bis(oxy))diundecanoic acid (0.170 g, 0.253 mmol) obtained in Reference Example 3 was dissolved in dichloromethane (3 mL), and (Z)-non-2-en-1-ol (manufactured by Tokyo Chemical Industry Co., Ltd., 0.169 mL, 1.01 mmol), 1-ethyl-3-(3-dimethylaminopropyl)carbodiimide hydrochloride (0.194 g, 1.01 mmol) and N,N-dimethyl-4-aminopyridine (0.0620 g, 0.505 mmol) were successively added thereto, followed by stirring at room temperature for 1 hour. Water was added to the resultant reaction mixture, and the aqueous layer was extracted with ethyl acetate. The organic layer was washed with saturated saline, dried over anhydrous magnesium sulfate, and then filtered and concentrated under reduced pressure. The obtained residue was purified by the silica gel column chromatography (hexane/ethyl acetate=95/5 to 70/30) to obtain compound IIc''-1 (0.188 g, yield: 49%).
ESI-MS m/z: 921 (M+H)$^+$;

Example 5

Di((Z)-non-2-en-1-yl)11,11'-((2-methyl-2-(methylamino)propane-1,3-diyl)bis(oxy))diundecanoate (Compound 5)

Compound 5 (0.057 g, yield: 63%) was obtained in the same way as in Example 3 by using di((Z)-non-2-en-1-yl) 11,11'-((2-methyl-2-((N-methyl-2-nitrophenyl)sulfonamide)propane-1,3-diyl)bis(oxy))diundecanoate obtained in Reference Example 4 instead of N-methyl-N-(2-methyl-1,3-bis((9Z,12Z)-octadeca-9,12,-dien-1-yloxy)propan-2-yl)-2-nitrobenzenesulfonamide.
ESI-MS m/z: 736 (M+H)$^+$; $^1$H-NMR (CDCl$_3$) δ: 0.88 (t, J=6.8 Hz, 6H), 1.02 (s, 3H), 1.24-1.40 (m, 42H), 1.50-1.66 (m, 14H), 2.06-2.13 (m, 4H), 2.30 (t, J=7.2 Hz, 4H), 2.32 (s, 3H), 4.62 (d, J=6.6 Hz, 4H), 5.48-5.56 (m, 2H), 5.60-5.68 (m, 2H).

Reference Example 5

Dinonyl 11,11'-((2-methyl-2-((N-methyl-2-nitrophenyl)sulfonamide)propane-1,3-diyl)bis(oxy))diundecanoate (Compound IIc''-2)

Compound IIc''-2 (0.090 g, yield: 39%) was obtained in the same way as in Reference Example 3 by using 1-nonenol (manufactured by Tokyo Chemical Industry Co., Ltd.) instead of (Z)-non-2-en-1-ol.
ESI-MS m/z: 925 (M+H)$^+$

Example 6

Dinonyl 11,11'-((2-methyl-2-(methylamino)propane-1,3-diyl)bis(oxy))diundecanoate (Compound 6)

Compound 6 (0.051 g, yield: 73%) was obtained in the same way as in Example 5 by using compound IIc"-2 obtained in Reference Example 5 instead of compound IIc"-1 obtained in Reference Example 4.

ESI-MS m/z: 740 (M+H)$^+$; $^1$H-NMR (CDCl$_3$) δ: 0.88 (t, J=7.0 Hz, 6H), 1.02 (s, 3H), 1.23-1.36 (m, 48H), 1.50-1.69 (m, 12H), 2.29 (t, J=7.5 Hz, 4H), 2.31 (s, 3H), 3.26 (s, 4H), 3.40 (t, J=6.7 Hz, 4H), 4.05 (t, J=6.8 Hz, 4H).

Example 7

A composition was prepared as follows using compound 2 obtained in Example 2. The nucleic acid used was anti-f7 siRNA silencing blood coagulation factor VII (hereinafter referred to as f7) gene and consisted of a sense strand [5'-CCCUGUCUUGGUUUCAAUUAA-3' (all sugars attached to the bases are ribose): SEQ ID NO: 1] and an antisense strand [5'-AAUUGAAACCAAGACAGGGUG-3' (all sugars attached to the bases are ribose; the 5' end is modified with a phosphoric acid group): SEQ ID NO: 2], and was obtained from Gene Design, Inc. (hereinafter, referred to as f7 siRNA). The nucleic acid was used after being adjusted to 24 mg/mL with distilled water.

Each sample was weighed to be compound 2/PEG-DMPE Na (manufactured by NOF Corp.)=57.3/5.52 mmol/L, and suspended in an aqueous solution containing hydrochloric acid and ethanol. A homogenous suspension was obtained by repeating stirring with a vortex stirring mixer and heating. This suspension was passed through a 0.05-μm polycarbonate membrane filter (manufactured by GE Healthcare Japan Ltd., Mode No. 800308) at room temperature to obtain a dispersion of compound 2/PEG-DMPE Na particles (liposomes). The average particle size of the obtained liposomes was measured with a particle size measurement apparatus to confirm that the average particle size fell within the range of 30 nm to 100 nm. The obtained liposome dispersion and the f7 siRNA solution were mixed at a ratio of liposome dispersion:f7 siRNA-1 solution=3:1. A 3-fold amount of distilled water was further added thereto and mixed to prepare a compound 2/PEG-DMPE Na/f7 siRNA-1 complex dispersion.

Meanwhile, each sample was weighed to be compound 2/PEG-DMPE Na (manufactured by NOF Corp.)/DSPC (manufactured by NOF Corp.)/cholesterol (manufactured by NOF Corp.)=8.947/0.147/5.981/14.355 mmol/L, and dissolved in ethanol to prepare a lipid membrane constituent solution.

The obtained lipid membrane constituent solution and the obtained compound 2/PEG-DMPE Na/f7 siRNA complex dispersion were mixed at a ratio of 1:1 and further mixed with a several-fold amount of distilled water to obtain a crude preparation.

The obtained crude preparation was concentrated using Amicon Ultra (manufactured by Merck Millipore), then diluted with physiological saline and filtered using a 0.2-μm filter (manufactured by Toyo Roshi Kaisha, Ltd.) in a clean bench. The siRNA concentration of the obtained composition was measured, and the composition was diluted with physiological saline according to an administration concentration to obtain a preparation (composition containing compound 2 and f7 siRNA).

Example 8

Preparations (compositions containing compounds 3 and f7 siRNA) were obtained in the same way as in Example 7 using compound 3 obtained in Example 3.

Comparative Example 1

A preparation was prepared in the same way as in Example 7 except that compound 2 was changed to N,N-dimethyl-N-(2-((9Z,12Z)-octadeca-9,12-dienyloxy)-1-(((9Z,12Z)-octadeca-9,12-dienyloxy)methyl)ethyl)amine (compound A) synthesized by the method described in Patent Literature 3.

Comparative Example 2

A preparation was prepared in the same way as in Example 7 except that compound 2 was changed to 2-dimethyl-3-[{(9Z,12Z)-octadeca-9,12-dien-1-yl}oxy]-2-([{(9Z,12Z)-octadeca-9,12-dien-1-yl}oxy]methyl)propane-1-ol (compound B) synthesized by the method described in Patent Literature 4.

The structures of compounds A and B are shown in Table 3.

TABLE 2

| Compound No. | Structure |
|---|---|
| A | (structure image) |
| B | (structure image) |

The average particle sizes of the preparations (compositions) obtained in Examples 7 and 8, and Comparative Examples 1 and 2 were measured using a particle size measurement apparatus. The results are shown in Table 3.

TABLE 3

|  | Example 7 | Example 8 | Comparative Example 1 | Comparative Example 2 |
|---|---|---|---|---|
| Particle size of obtained preparation (nm) | 114 | 104 | 99 | 106 |

Test Example 1

The preparations (compositions containing compounds 2, 3, A and B, respectively, and f7 siRNA) obtained in Examples 7 and 8, and Comparative Examples 1 and 2 were each subjected to an in vivo drug efficacy evaluation test by a method given below. Each preparation was used after being diluted with physiological saline according to the test.

Mice (Balb/c, obtained from CLEA Japan, Inc.) were acclimatized and raised. Then, each preparation was intravenously administered at 0.03 and/or 0.3 mg/kg in terms of the siRNA concentration to the mice. 48 hours after the administration, blood was collected, and the collected blood was centrifuged at 8000 rpm at 4° C. for 8 minutes using a high-speed refrigerated microcentrifuge (TOMY MX305; manufactured by Tomy Seiko Co., Ltd.). Absorbance in standard solutions and the plasma samples was measured in ARVO (405 nm) using BIOPHEN VII kit (manufactured by ANIARA, cat #: A221304) according to the method described in the instruction manual of the product. A calibration curve was prepared from the obtained absorbance, and the factor VII protein concentration in plasma was calculated. n=3 for each group.

The results about the calculated factor VII protein concentration in plasma are shown in FIG. 1.

As is evident from FIG. 1, the expression of the factor VII gene was strongly suppressed by the administration of each of the preparations (compositions containing compounds 2 and 3, respectively, and f7 siRNA) obtained in Examples 7 and 8. Also, each of the preparations obtained in Examples 7 and 8 more strongly suppressed the expression of the factor VII gene than preparations (compositions containing compounds A and B, respectively, and f7 siRNA) obtained in Comparative Examples 1 and 2.

These results demonstrated that the composition of the present invention can introduce a nucleic acid into a cell or the like, and the compound of the present invention facilitates delivering a nucleic acid into a cell in vivo.

Example 9

A composition was prepared as follows using compound 5 obtained in Example 5. The nucleic acid used was anti-HPRT1 siRNA silencing hypoxanthine-guanine phosphoribosyltransferase 1 (hereinafter referred to as HPRT1) gene and consisted of a sense strand [5'-rGrCrCrArGrArCrUrU-rUrGrUrUrGrGrArUrUrUrGrA-3' (sugars attached to the bases with r are ribose)] (SEQ ID NO:3) and an antisense strand [5''-rArAmArUmCrCmArAmCrAmArAmGrUm-CrUmGrGmCmUmU-3'' (sugars attached to the bases with r and m are ribose, and ribose with the hydroxy group at position 2'' substituted with methoxy group, respectively] (SEQ ID NO:4), and was obtained from Gene Design, Inc. (hereinafter, referred to as HPRT1 siRNA). The nucleic acid was used after being adjusted to 24 mg/mL with distilled water.

Each sample was weighed to be compound 5/PEG-DMPE Na (manufactured by NOF Corp.)=57.3/5.52 (all in units of mmol/L), and suspended in an aqueous solution containing hydrochloric acid and ethanol, and a homogenous suspension was obtained by repeating stirring with a vortex stirring mixer and heating. This suspension was passed through a 0.05-□m polycarbonate membrane filter (manufactured by GE Healthcare Japan Ltd.) at room temperature to obtain a dispersion of compound 5/PEG-DMPE Na particles (liposomes). The average particle size of the obtained liposomes was measured with a particle size measurement apparatus (manufactured by Malvern Panalytical Ltd., Zetasizer Nano ZS) to confirm that the average particle size fell within the range of 30 nm to 100 nm. The obtained liposome dispersion and the HPRT1 siRNA solution were mixed at a ratio of liposome dispersion:HPRT1 siRNA solution=3:1, and a 29-fold amount of distilled water was further added thereto and mixed to prepare a compound 5/PEG-DMPE Na/HPRT1 siRNA complex dispersion.

Meanwhile, each sample was weighed to be compound 5/PEG-DMPE Na (manufactured by NOF Corp.)/cholesterol (manufactured by NOF Corp.)=8.947/0.147/20.336 (all in units of mmol/L), and dissolved in ethanol to prepare a lipid membrane constituent solution.

A 4-fold amount of ethanol was added to the obtained lipid membrane constituent solution, the resultant lipid membrane constituent solution and the compound 5/PEG-DMPE Na/HRPT1 siRNA complex dispersion were mixed at a ratio of 2:3 and further mixed with a several-fold amount of distilled water to obtain a crude preparation.

The obtained crude preparation was concentrated using Amicon Ultra (manufactured by Merck Millipore), then diluted with physiological saline and filtered using a 0.2-□m filter (manufactured by Toyo Roshi Kaisha, Ltd.) in a clean bench. The siRNA concentration of the obtained composition was measured, and the composition was diluted with physiological saline according to an appropriate concentration to obtain a preparation (composition containing compound 5 and HPRT1 siRNA).

Example 10

A preparation (composition containing compound 6 and HPRT1 siRNA) was obtained in the same way as in Example 9 by using compound 6 obtained in Example 6.

The average particle sizes of the preparations (compositions) obtained in Examples 9 and 10 were measured using a particle size measurement apparatus, and the results are shown in Table 4.

TABLE 4

|  | Example 9 | Example 10 |
|---|---|---|
| Particle size of obtained preparation (nm) | 105 | 115 |

Test Example 2: Evaluation Test of Preparation for In Vitro Activity in Human Lung Fibroblast Cell Line In order to check the activity of the preparations obtained in Examples 9 and 10, evaluation was performed by the following method.

A human lung fibroblast cell line, Normal Human Lung Fibroblasts (manufactured by Lonza, CC-2512) was seeded in DMEM medium (manufactured by Thermo Fisher Scientific) containing 15% fetal bovine serum (FBS) and 1% penicillin-streptomycin (manufactured by Thermo Fisher Scientific) at 4000 cells/100 µL/well, and cultured for 22 to 24 hours under conditions of 37° C. and 5% $CO_2$. Thereafter, each preparation prepared in Examples 9 and 10 was prepared to have a siRNA concentration of 5 nM or 25 nM after addition, and added to the cells in an amount of 100 µL. Also, as a negative control, 100 µL of the DMEM medium containing 15% FBS and 1% penicillin-streptomycin was added to the cells.

The cells treated with each of the preparations were cultured in a 5% $CO_2$ incubator at 37° C. for 24 hours, and washed with ice-cooled PBS, and total RNA was recovered by using TaqMan Fast Cells-to-CT kit (manufactured by Thermo Fisher Scientific, 4399003) in accordance with instructions attached thereto to produce cDNA.

The obtained cDNA was used as a template for PCR reaction to perform PCR amplification specific to the HPRT1 gene and constitutive expression gene of PPIA (peptidylprolyl isomerase A) gene using Applied Biosystems QuantStudio 12K Flex, TaqMan Fast Universal PCR Master Mix (2×) (manufactured by Applied Biosystems, Inc., 4352042) and TaqMan probe (TaqMan® Gene Expression Assays, HPRT1: Hs02800695_m1, PPIA: Hs04194521_s1) to quantitatively determine the amount of mRNA. Conditions for the PCR reaction were set in accordance with instructions attached to TaqMan Fast Universal PCR Master Mix (2×). The amount of mRNA of HPRT1 against the amount mRNA of PPIA was calculated, and a calculated value of a negative control group was assumed as 1 to calculate the amount of mRNA of each sample as a relative ratio. The results of the amount of mRNA of HPRT1 are shown in Table 5.

TABLE 5

| | HPRT1 mRNA (Suppression Ratio %) | |
|---|---|---|
| | Dose | |
| Example | 25 nmol/L | 5 nmol/L |
| 9 | 88 | 83 |
| 10 | 82 | 59 |

As is evident from Table 5, the expression of the HPRT1 gene was strongly suppressed by adding each the preparations obtained in Examples 9 and 10.

These results demonstrated that the composition of the present invention can introduce a nucleic acid into a cell or the like, and that the compound of the present invention facilitates delivering a nucleic acid into a cell in vitro.

INDUSTRIAL APPLICABILITY

A compound or a pharmaceutically acceptable salt thereof and a composition of the present invention are industrially applicable as, for example, a medicament because they can easily introduce a nucleic acid into a cell or the like when administered to a mammal or the like.

Free Text of Sequence Listing

SEQ ID NO: 1 shows siRNA sense strand of blood coagulation factor VII.

SEQ ID NO: 2 shows siRNA antisense strand of blood coagulation factor VII.

SEQ ID NO: 3 shows siRNA sense strand of hypoxanthine-guanine phosphoribosyltransferase 1.

SEQ ID NO: 4 shows siRNA antisense strand of hypoxanthine-guanine phosphoribosyltransferase 1.

The invention claimed is:

1. A compound represented by formula (I), or a pharmaceutically acceptable salt thereof:

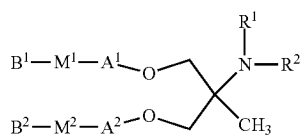

(I)

wherein $R^1$ and $R^2$ are a hydrogen atom or C1-C3 alkyl;
$A^1$ and $A^2$ are linear or branched C8-C20 alkylene or C8-C20 alkenylene;
$M^1$ and $M^2$ are selected from the group consisting of —C=C—, —OC(O)—, —C(O)O—, —SC(O)—, —C(O)S—, —OC(S)—, —C(S)O—, —SS—, —C($R^5$)=N—, —N=C($R^5$)—, —C($R^5$)=N—O—, —O—N=C($R^5$)—, —N($R^5$)C(O)—, —C(O)N($R^5$)—, —N($R^5$)C(S)—, —C(S)N($R^5$)—, —N($R^5$)C(O)N ($R^6$)—, —N($R^5$)C(O)O—, —OC(O)N($R^5$)—, and —OC(O)O—;

$R^5$ and $R^6$ are a hydrogen atom or C1-C3 alkyl; and
$B^1$ and $B^2$ are linear or branched C1-C16 alkyl or C2-C16 alkenyl.

2. The compound according to claim 1, or a pharmaceutically acceptable salt thereof, wherein $R^1$ and $R^2$ are a hydrogen atom or methyl.

3. The compound according to claim 1, or a pharmaceutically acceptable salt thereof, wherein $A^1$ and $A^2$ are linear or branched C8-C12 alkylene or C10-C14 alkenylene.

4. The compound according to claim 1, or a pharmaceutically acceptable salt thereof, wherein $M^1$ and $M^2$ are selected from the group consisting of —C=C—, —OC(O)—, and —C(O)O—.

5. The compound according to claim 1, or a pharmaceutically acceptable salt thereof, wherein $B^1$ and $B^2$ are linear or branched C2-C9 alkyl or C3-C9 alkenyl.

6. The compound according to claim 1, or a pharmaceutically acceptable salt thereof, wherein $B^1$-$M^1$-$A^1$ and $B^2$-$M^2$-$A^2$ are selected from the group consisting of (Z)-tetradec-9-enyl, (Z)-hexadec-9-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, and (Z)-docos-13-enyl.

7. The compound according to claim 1, or a pharmaceutically acceptable salt thereof, wherein $B^1$-$M^1$-$A^1$ and $B^2$-$M^2$-$A^2$ are selected from the group consisting of (Z)-hexadec-9-enyl, (Z)-octadec-9-enyl, (9Z,12Z)-octadeca-9,12-dienyl, and (11Z,14Z)-icosa-11,14-dienyl.

8. The compound according to claim 1 or a pharmaceutically acceptable salt thereof,
wherein $B^1$-$M^1$-$A^1$ and $B^2$-$M^2$-$A^2$ are selected from the following structures:

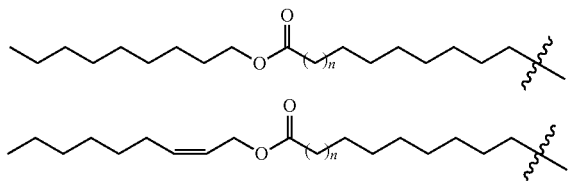

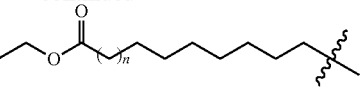

wherein n is an integer from 1 to 4.

9. The compound according to claim 1, or a pharmaceutically acceptable salt thereof, wherein $B^1$-$M^1$-$A^1$ and $B^2$-$M^2$-$A^2$ are the same.

10. A composition, comprising the compound according to claim 1, or a pharmaceutically acceptable salt thereof, and a nucleic acid.

11. The composition according to claim 10, wherein the nucleic acid is a nucleic acid having a silencing effect on a target gene through the use of RNA interference (RNAi).

12. The composition according to claim 11, wherein the target gene is a gene related to tumor.

13. The composition according to claim 11, wherein the target gene is a gene expressed in the liver, the lung, the kidney, or the spleen.

14. A medicament, comprising the composition according to claim 10.

15. A method for introducing the nucleic acid into a cell using the composition according to claim 10.

16. A treatment method for a disease related to the liver, the lung, the kidney or the spleen, comprising a step of administering the composition according to claim 10 to a human.

17. The treatment method according to claim 16, wherein the composition is intravenously administered.

* * * * *

SEQUENCE LISTING

```
<160> NUMBER OF SEQ ID NOS: 4

<210> SEQ ID NO 1
<211> LENGTH: 21
<212> TYPE: RNA
<213> ORGANISM: Artificial Sequence
<220> FEATURE:
<223> OTHER INFORMATION: Blood Coagulation Factor VII siRNA sense

<400> SEQUENCE: 1
cccugucuug guuucaauua a                                            21

<210> SEQ ID NO 2
<211> LENGTH: 21
<212> TYPE: RNA
<213> ORGANISM: Artificial Sequence
<220> FEATURE:
<223> OTHER INFORMATION: Blood Coagulation Factor VII siRNA antisense
<220> FEATURE:
<221> NAME/KEY: misc_feature
<222> LOCATION: (1)..(1)
<223> OTHER INFORMATION: 5'-O-phosphorylated Adenine

<400> SEQUENCE: 2
nauugaaacc aagacagggu g                                            21

<210> SEQ ID NO 3
<211> LENGTH: 21
<212> TYPE: RNA
<213> ORGANISM: Artificial Sequence
<220> FEATURE:
```

```
<223> OTHER INFORMATION: HPRT1 siRNA sense

<400> SEQUENCE: 3
gccagacuuu guuggauuug a                                               21

<210> SEQ ID NO 4
<211> LENGTH: 21
<212> TYPE: RNA
<213> ORGANISM: Artificial Sequence
<220> FEATURE:
<223> OTHER INFORMATION: HPRT1 siRNA antisense
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: 2'-O-methyladenosine
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(21)
<223> OTHER INFORMATION: um

<400> SEQUENCE: 4
aaauccaaca aagucuggcu u                                               21
```